US006839588B1

(12) United States Patent
Rudy

(10) Patent No.: US 6,839,588 B1
(45) Date of Patent: Jan. 4, 2005

(54) ELECTROPHYSIOLOGICAL CARDIAC MAPPING SYSTEM BASED ON A NON-CONTACT NON-EXPANDABLE MINIATURE MULTI-ELECTRODE CATHETER AND METHOD THEREFOR

(75) Inventor: Yoram Rudy, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/463,427

(22) PCT Filed: Jul. 29, 1998

(86) PCT No.: PCT/US98/15712

§ 371 (c)(1),
(2), (4) Date: Mar. 29, 2000

(87) PCT Pub. No.: WO99/06112

PCT Pub. Date: Feb. 11, 1999

Related U.S. Application Data

(60) Provisional application No. 60/054,342, filed on Jul. 31, 1997.

(51) Int. Cl.[7] .............................................. A61B 5/0402
(52) U.S. Cl. ...................... 600/523; 600/508; 607/119
(58) Field of Search ................................. 607/119, 122; 600/508, 507, 510, 523

(56) References Cited

U.S. PATENT DOCUMENTS

| | | |
|---|---|---|
| 4,203,451 A | 5/1980 | Panico |
| 4,535,783 A | 8/1985 | Marangoni |
| 4,649,924 A | 3/1987 | Taccardi |
| 4,805,631 A | 2/1989 | Roi du Maroc, II. |
| 4,991,580 A | 2/1991 | Moore |
| 4,991,587 A | 2/1991 | Blakeley et al. |
| 5,020,540 A | 6/1991 | Chamoun |
| 5,042,499 A | 8/1991 | Frank et al. |
| 5,086,776 A | 2/1992 | Fowler, Jr. et al. |
| 5,161,539 A | 11/1992 | Evans et al. |
| 5,297,549 A | 3/1994 | Beatty et al. |
| 5,311,873 A | 5/1994 | Savard et al. |
| 5,433,198 A * | 7/1995 | Desai .......................... 607/122 |
| 5,483,968 A | 1/1996 | Adam et al. |
| 5,487,391 A | 1/1996 | Panescu |
| 5,503,149 A | 4/1996 | Beavin |
| 5,553,611 A | 9/1996 | Budd et al. |
| 5,568,809 A | 10/1996 | Ben-haim |
| 5,680,860 A * | 10/1997 | Imran .......................... 600/374 |
| 5,938,694 A * | 8/1999 | Jaraczewski et al. ....... 607/122 |

OTHER PUBLICATIONS

Lin ZW, Jia P., Ershler PR, , Taccardi B., Lux RL, Khoury, DS, Rudy Y., "Noncontact Endocardial Mapping: Reconstruction of Electrograms and Isochrones From Interacavitary Probe Potentials".*Journal of Cardiovascular Electrophysiology*, 1997; 8:415–431.

Jia P., "Noncontact catheter for electrophysiological cardia mapping", Case Western Reserve University, Department of Biomedical Engineering, Jan. 1998.

(List continued on next page.)

Primary Examiner—George R. Evanisko
(74) Attorney, Agent, or Firm—Kevin A. Oliver; Foley Hoag LLP

(57) ABSTRACT

A system (10) for determining electrical potentials on an endocardial surface of a heart is provided. The system includes a non-contact, non-expandable, miniature, multi-electrode catheter probe (12), a plurality of electrodes (32) disposed on an end portion (30) thereof, means for determining endocardial potentials (14) based on electrical potentials measured by the catheter probe, a matrix of coefficients that is generated based on a geometric relationship between the probe surface, and the endocardial surface. A method is also provided.

12 Claims, 37 Drawing Sheets

OTHER PUBLICATIONS

Liu ZW, "Inverse reconstruction of endocardial potentials, electrograms and activation sequences from intracavitary probe potential measurements", Case Western Reserve University, Department of Biomedical Engineering, Aug. 1996.

Khoury DS, B. Taccardi, Lux RUL, Ershler PR, Rudy Y., "Reconstruction of endocardial potentials and activation sequences from intracavitary probe measurements". Circulation 1995; 91:845–863.

Rudy Y, Messinger–Rapport BJ, The inverse problem in electrocardiography solutions in terms of epicardial potentials,: *CRC Crit Rev Biomed Eng.*, 16:215–268 (1988).

Rudy Y, Oster HS, "The electrocardiographic inverse problem, " *CRC Crit Rev Biomed Eng.*, 20:25–46 (1992).

Messinger–Rapport BJ, Rudy Y, "Computational issues of importance to the inverse recovery of epicardial potentials in a realistic heart–torso geometry," *Math Biosci*, 97:85–120 (1989) (published erratum in *Math Biosci*, 99(1):141 (Apr. 1990)).

Oster HS, Rudy Y, "The use of temporal information in the regularization of the inverse problem of a electrocardiography," *IEEE Trans Biomed Eng.*, 39:65–75 (1992).

Messinger, Rapport BJ, Rudy Y, "Regularization of the inverse problem in electrocardiography. A model study," *Math Biosci*, 89:79–118 (1988).

Colli–Franzone P., Guerri L., Taccardi B., Viganotti C., "Finite element approximation of regularized solutions of the inverse potential problem of electrocardiography and applications to experimental data", Calcolo 1985, 22:91–186.

Colli–Franzone P., Guerri L., Taccardi B., Viganotti C., "Mathematical procedure for solving the inverse problem of electrocardiography," *Math Biosci*, 77:353–96 (1985).

Rudy Y, Taccardi B, Noninvasive Imaging and Catheter Imaging of Potentials, Electrograms, and Isochrones on the Ventricular Surfaces, *Journal of Electrocardiology*, vol. 30 Supplement, (1998) pp. 19–23.

Oster HS, Rudy Y, "Regional Regularization of the Electrocardiographic Inverse Problem: A Model Study Using Spherical Geometry", *IEEE Transactions on Biomedical Engineering*, vol. 44, No. 2, Feb. 1997, pp. 188–199.

Burnes JE, Kaelber DC, Taccardi B, Lux RL, Ershler PH, Rudy Y, "A field–Compatible Method For Interpolating Biopotentials", *Annals of Biomedical Engineering*, vol. 26, pp. 37–47, 1998.

* cited by examiner

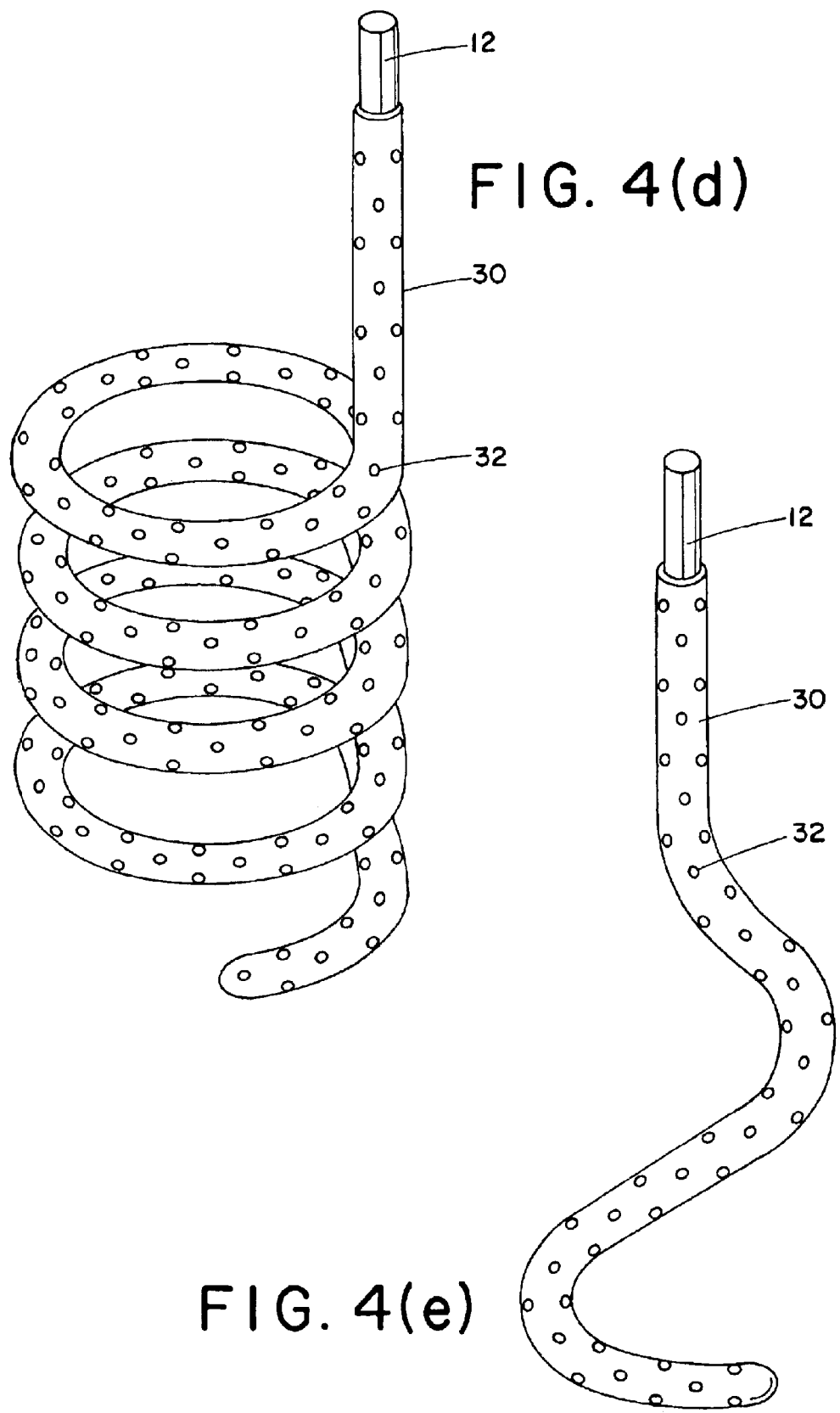

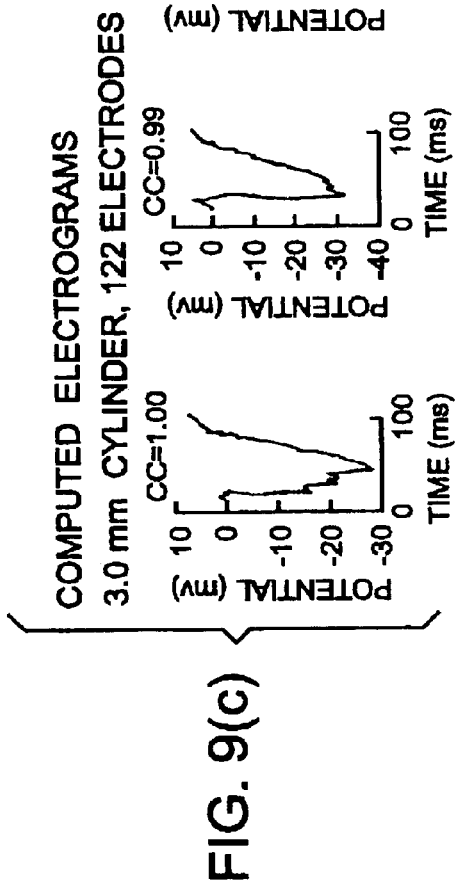
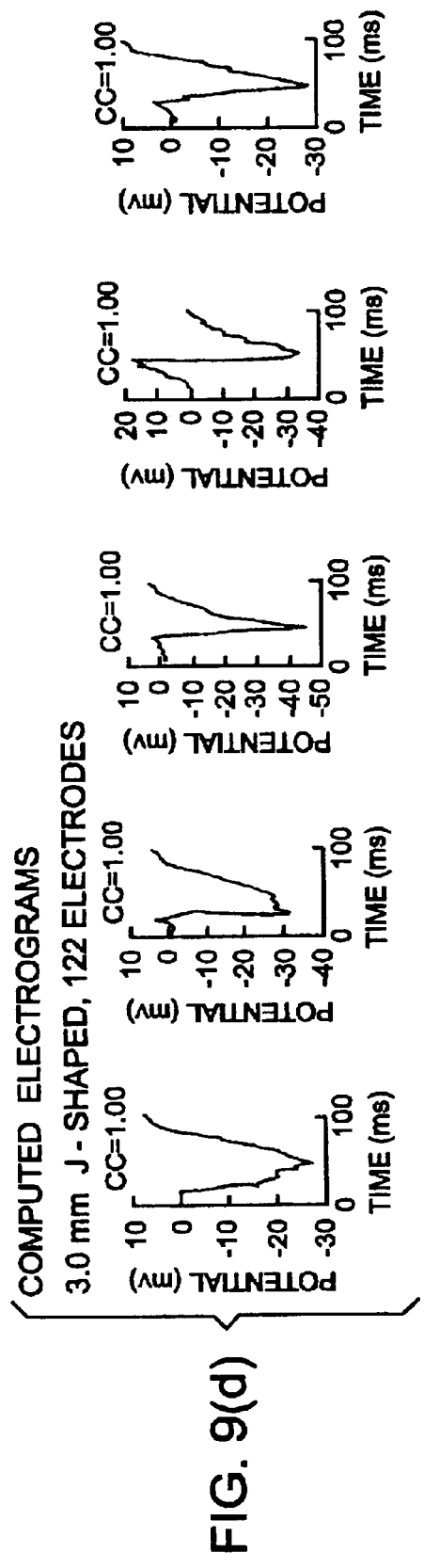
FIG. 9(c)
FIG. 9(d)

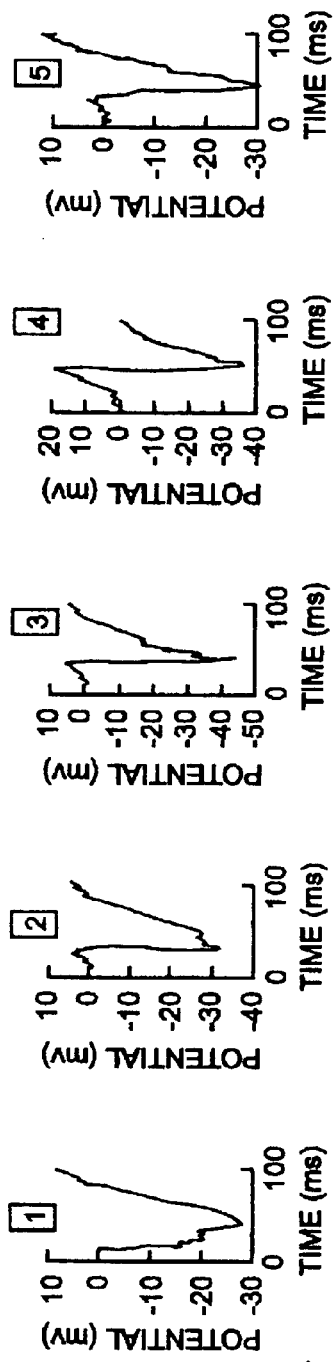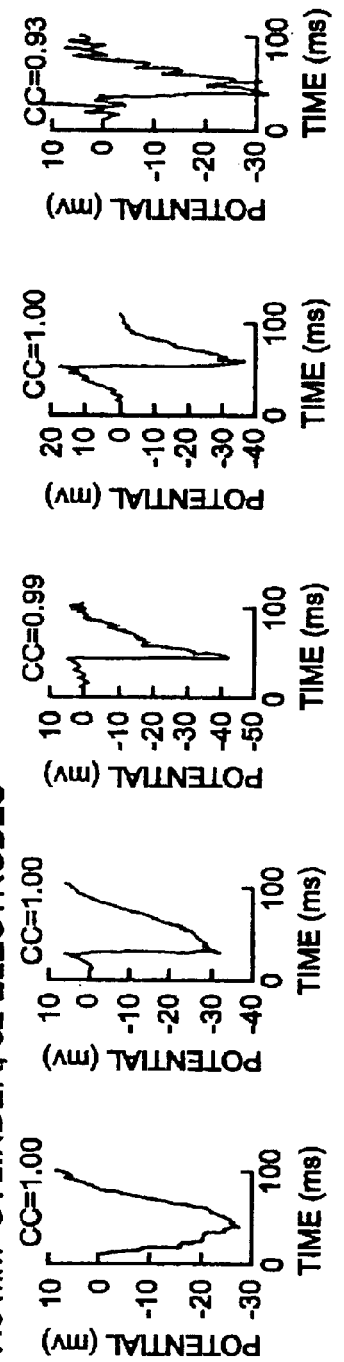
FIG. 10(a) EFFECTS OF NUMBER OF PROBE ELECTRODES ON ELECTROGRAMS
MEASURED ELECTROGRAMS
FIG. 10(b) COMPUTED ELECTROGRAMS
7.6 mm CYLINDER, 62 ELECTRODES

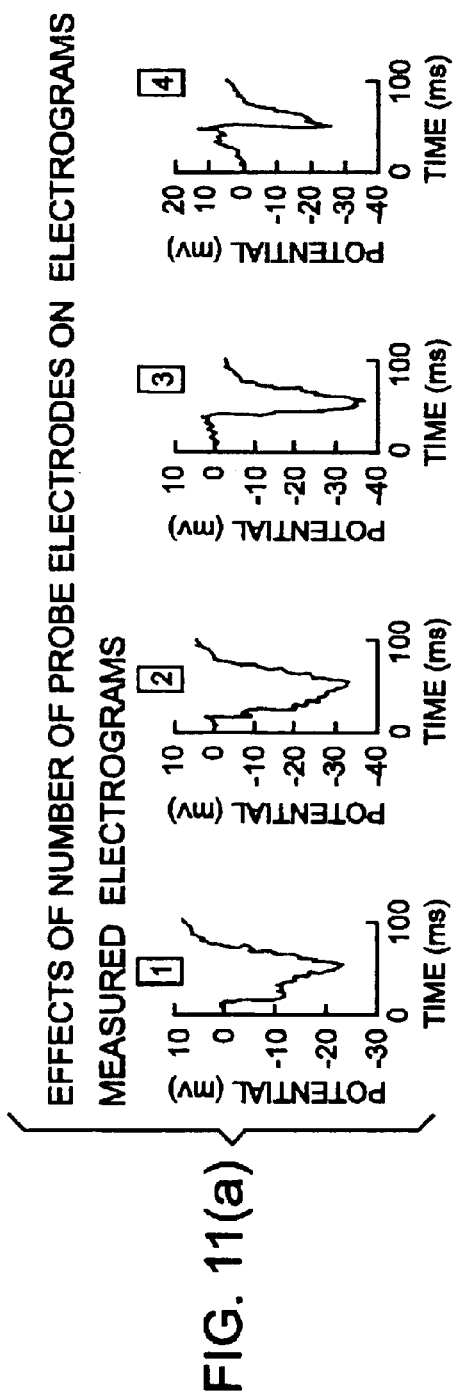
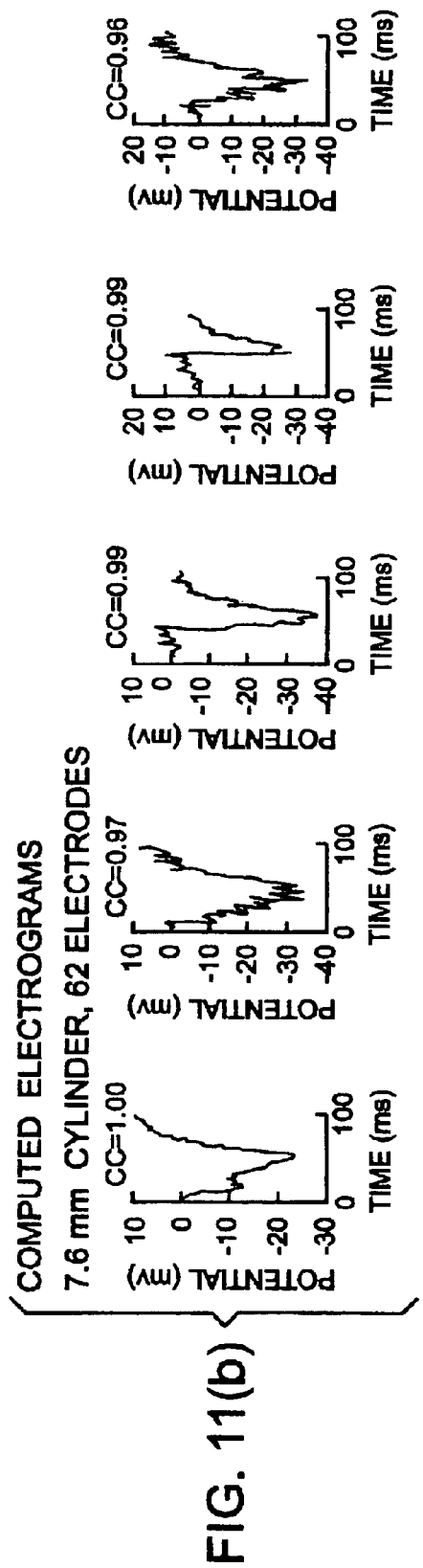
FIG. 11(a)
FIG. 11(b)

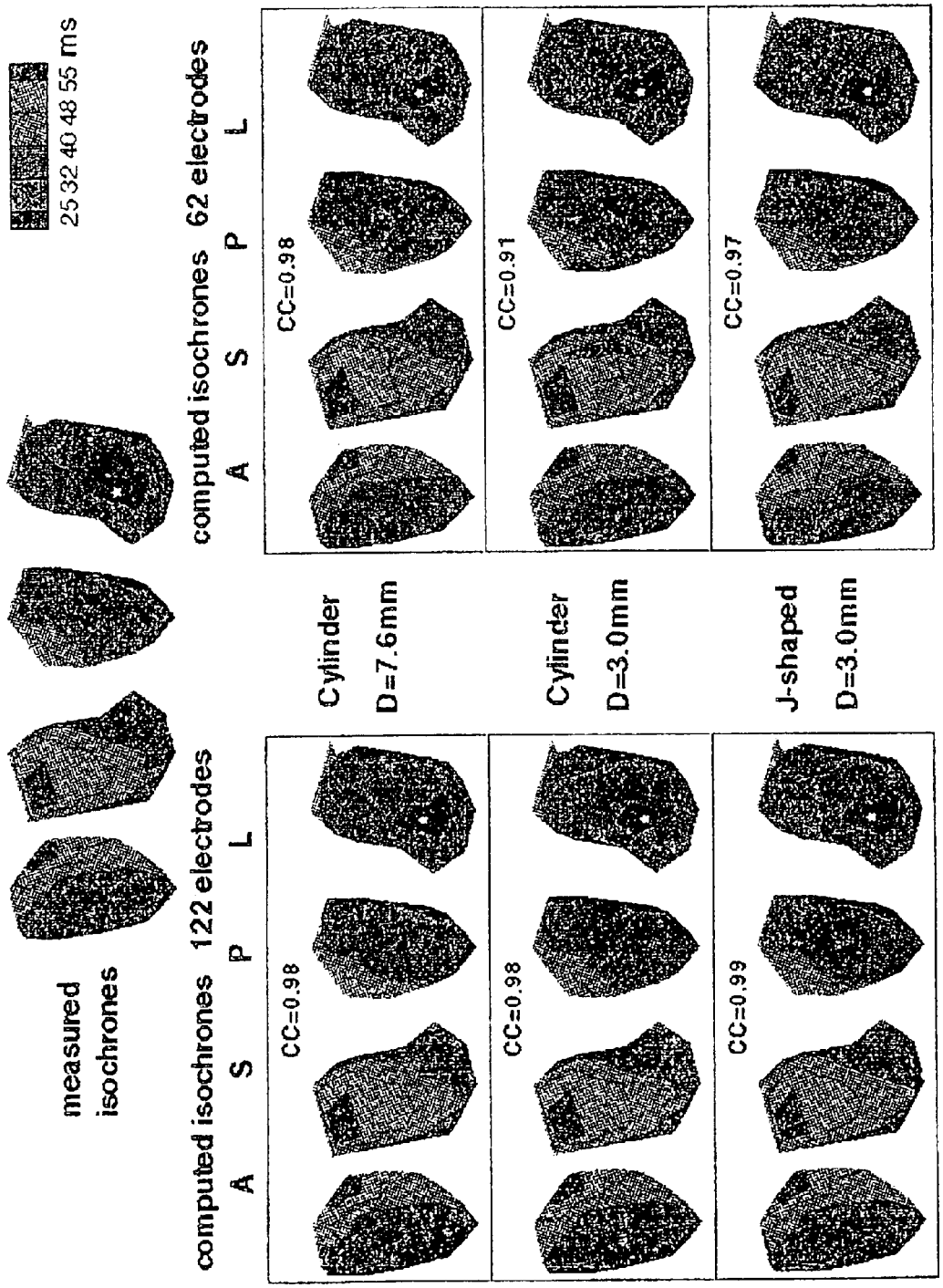
FIG. 12 EFFECTS OF NUMBER OF PROBE ELECTRODES ON ISOCHRONE MAP

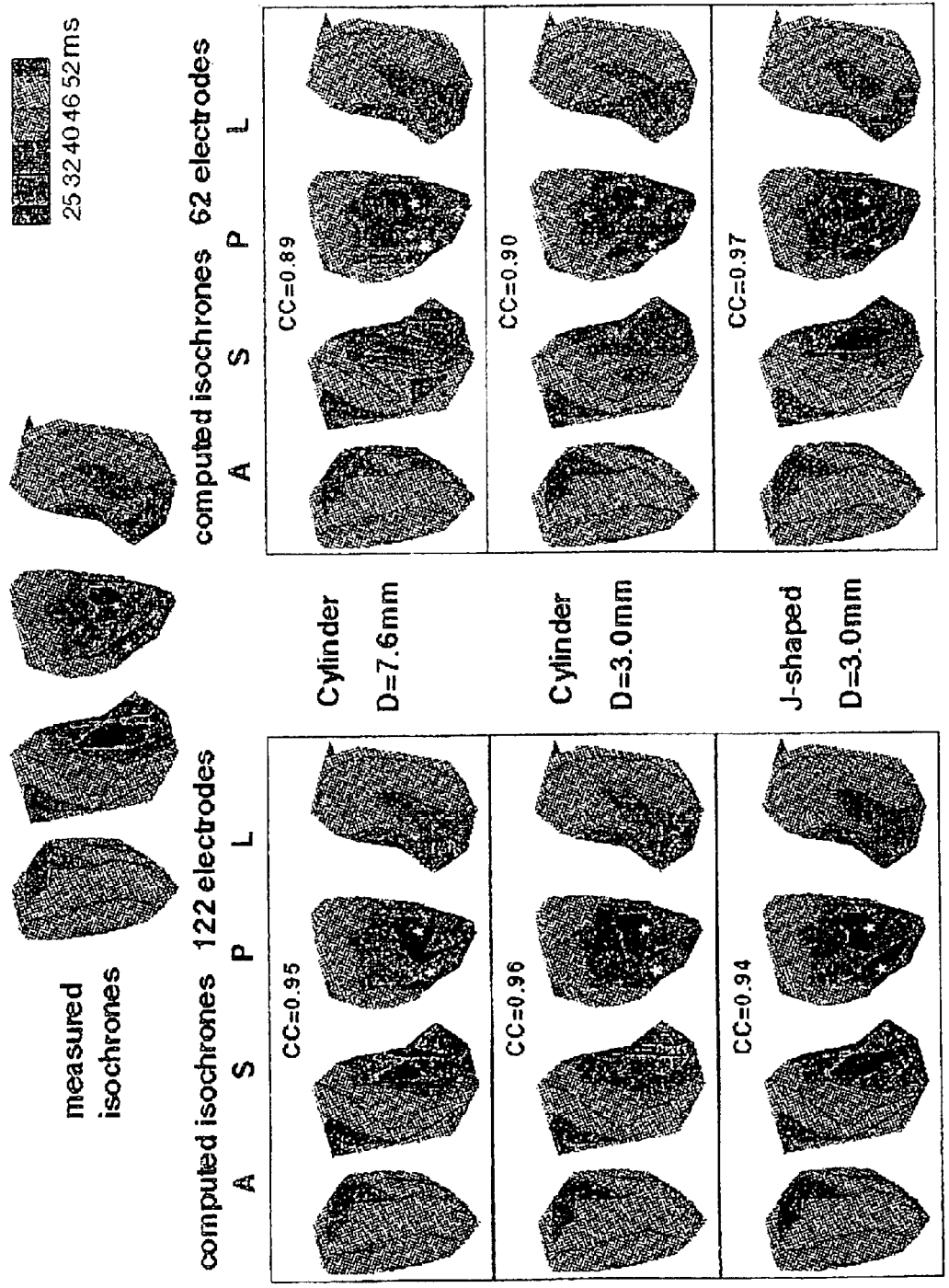
FIG. 13 EFFECTS OF NUMBER OF PROBE ELECTRODES ON ISOCHRONE MAP

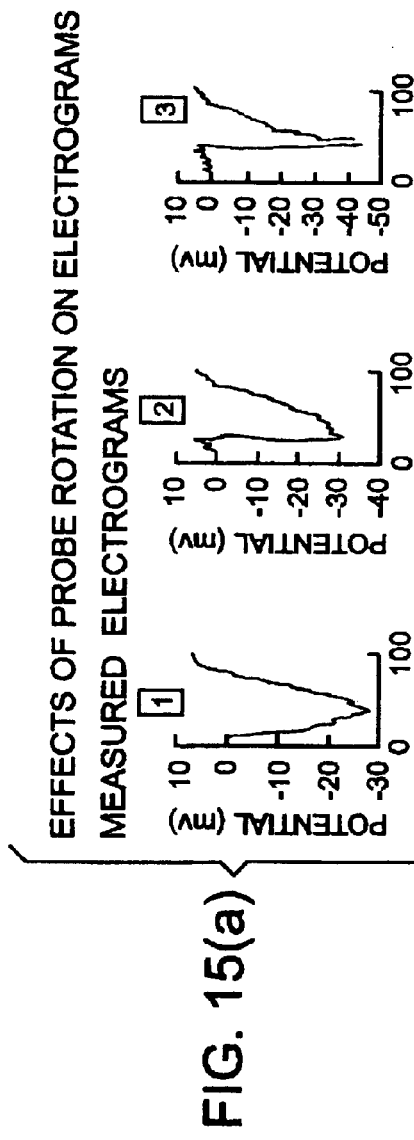
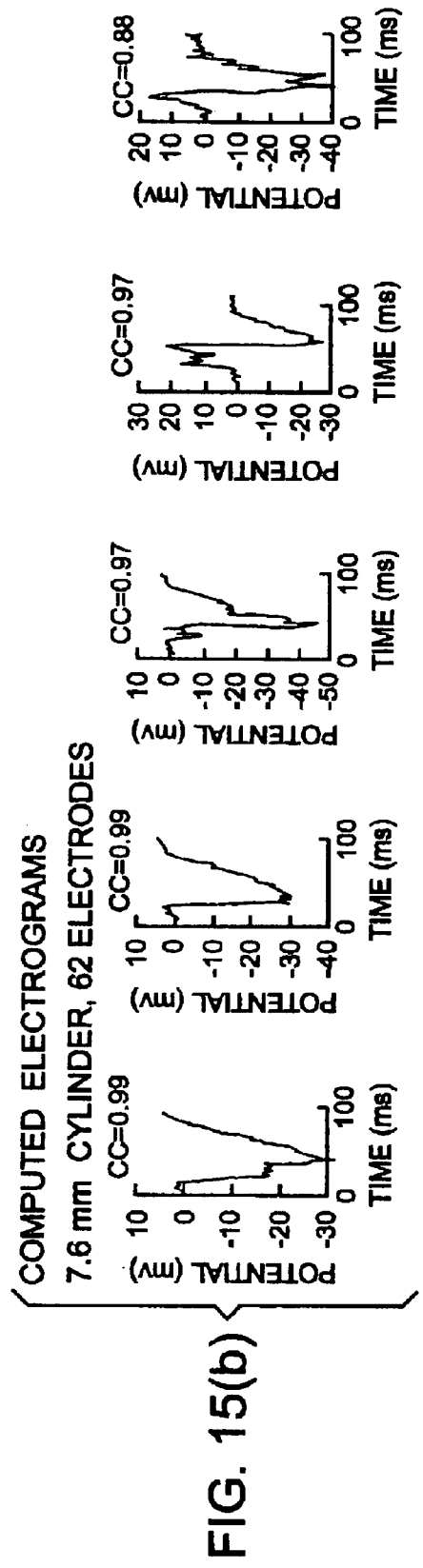
FIG. 15(a) EFFECTS OF PROBE ROTATION ON ELECTROGRAMS — MEASURED ELECTROGRAMS
FIG. 15(b) COMPUTED ELECTROGRAMS 7.6 mm CYLINDER, 62 ELECTRODES

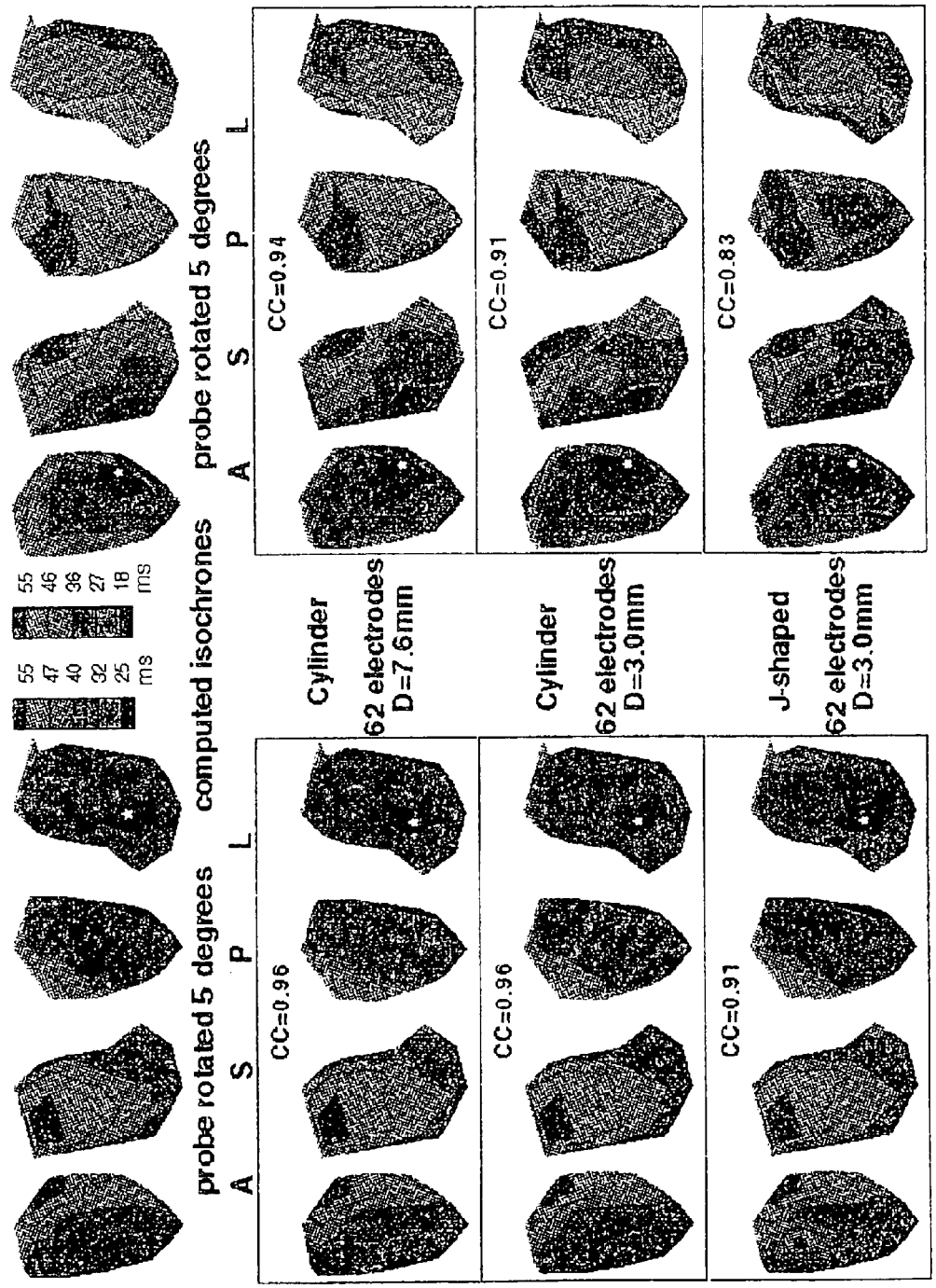
FIG. 16 EFFECTS OF PROBE ROTATION ON ISOCHRONE MAP

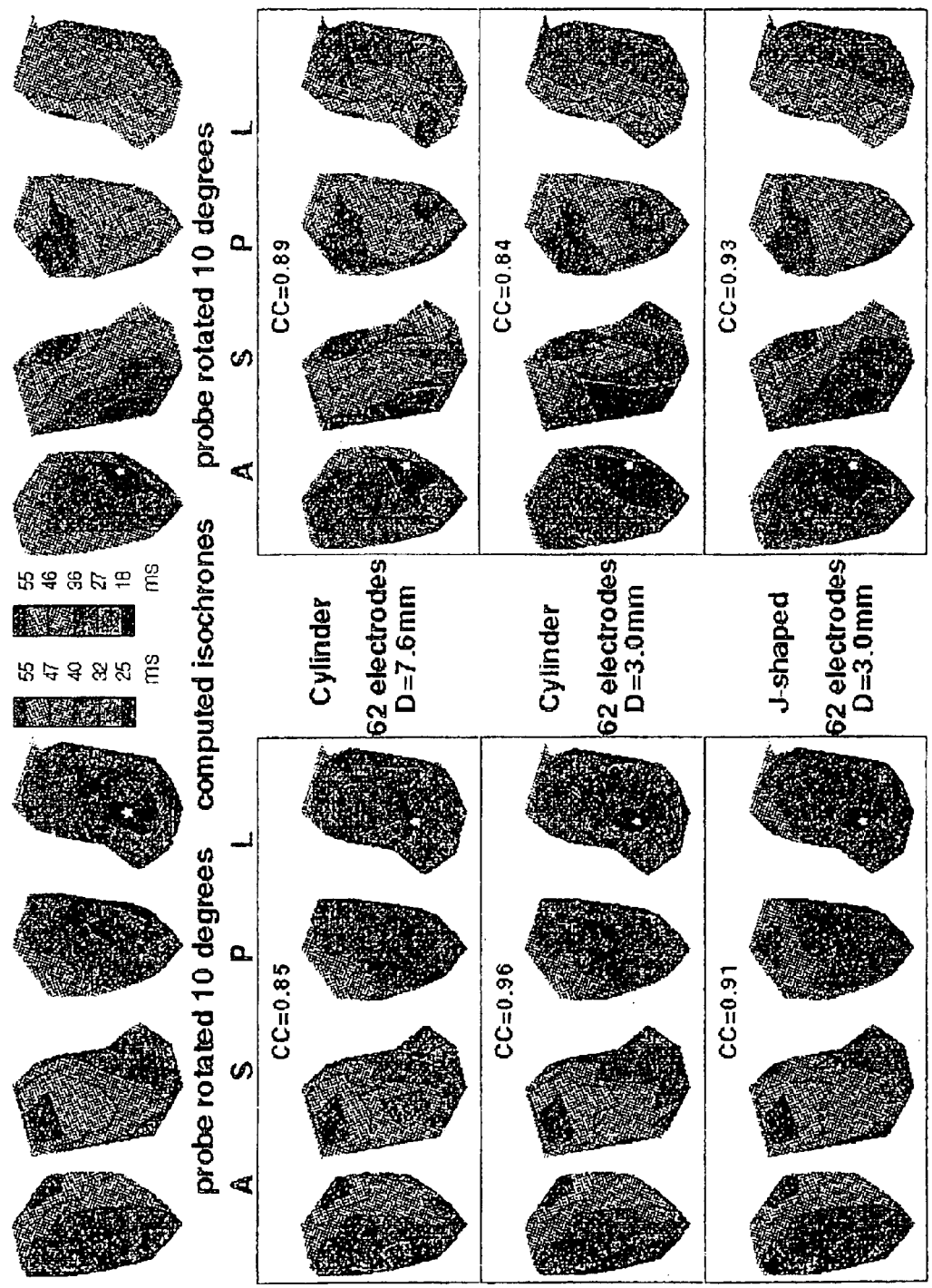
FIG. 17 EFFECTS OF PROBE ROTATION ON ISOCHRONE MAP

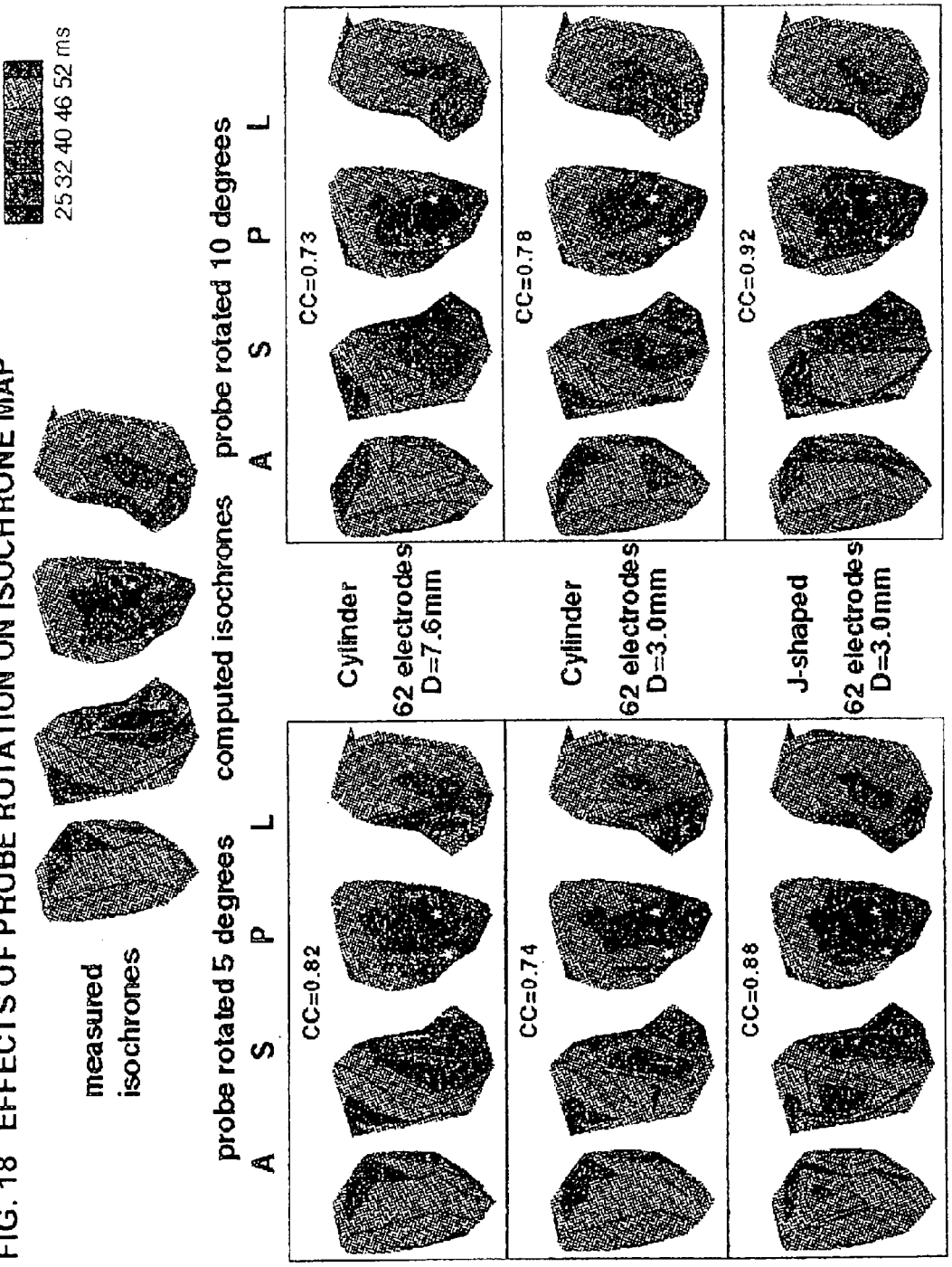
FIG. 18 EFFECTS OF PROBE ROTATION ON ISOCHRONE MAP

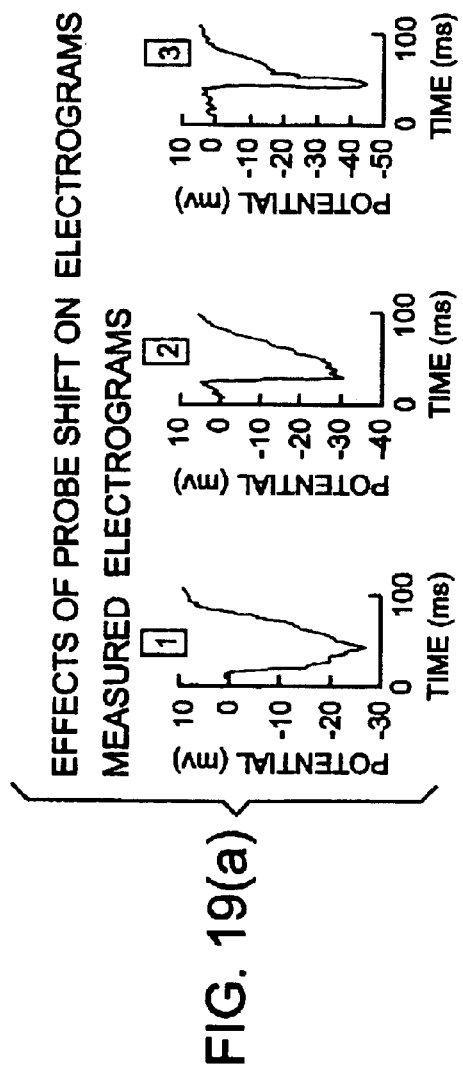
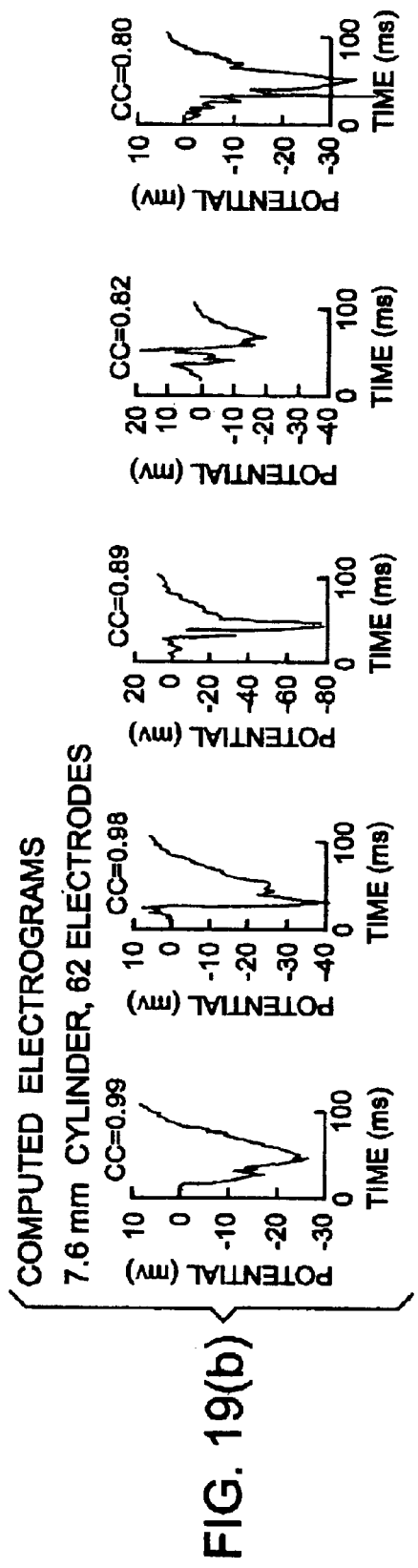
FIG. 19(a)
FIG. 19(b)

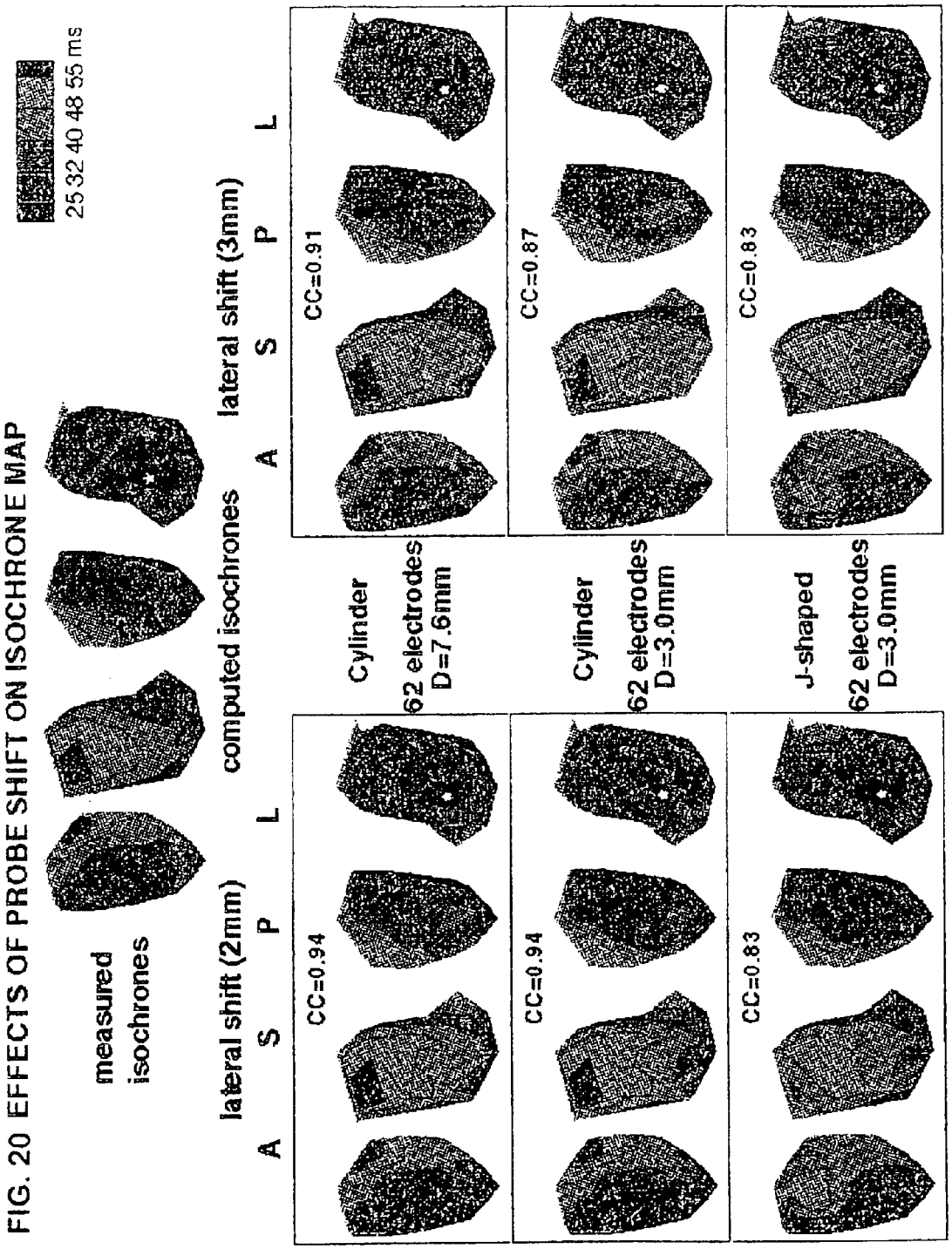
FIG. 20 EFFECTS OF PROBE SHIFT ON ISOCHRONE MAP

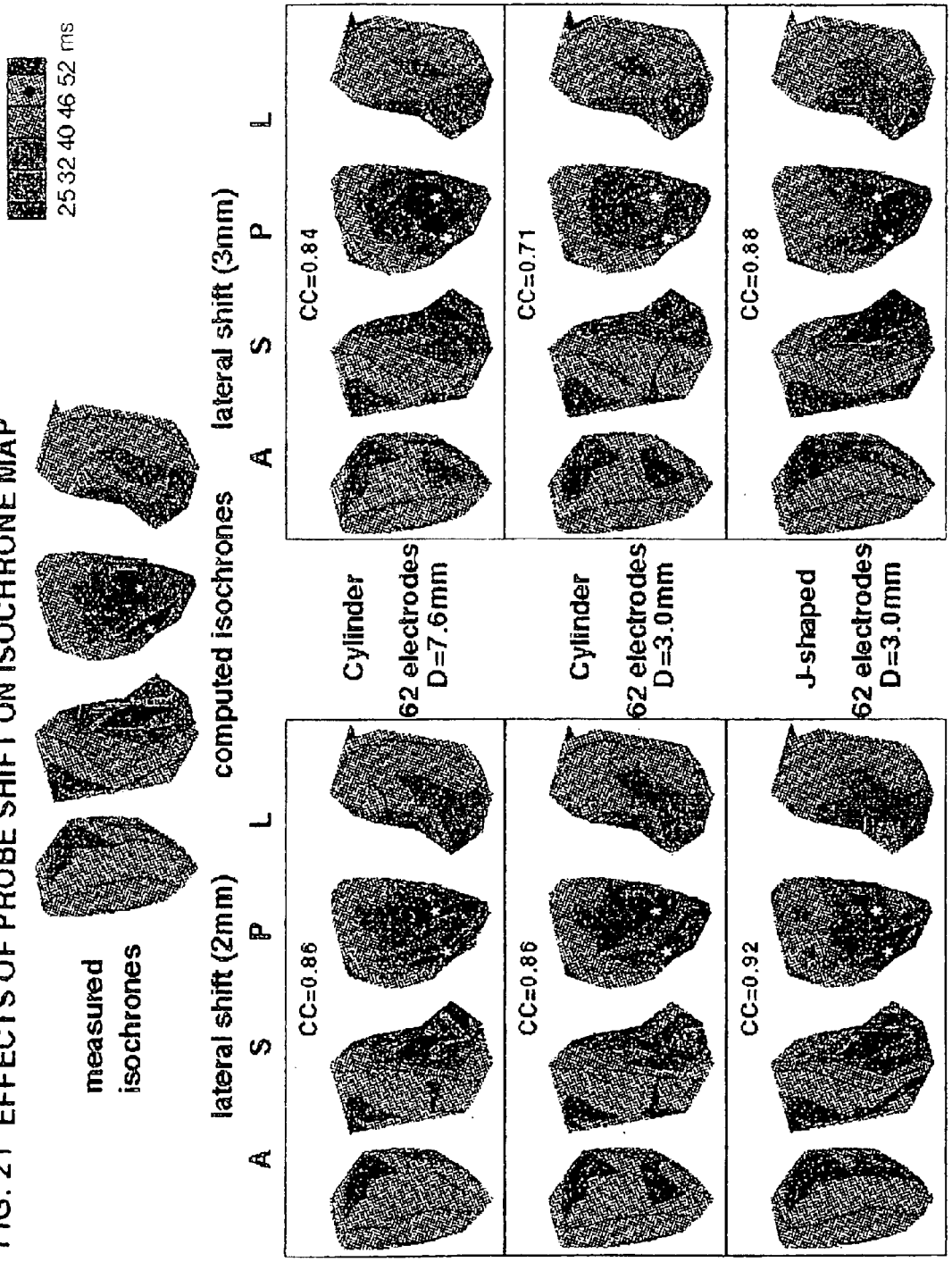
FIG. 21 EFFECTS OF PROBE SHIFT ON ISOCHRONE MAP

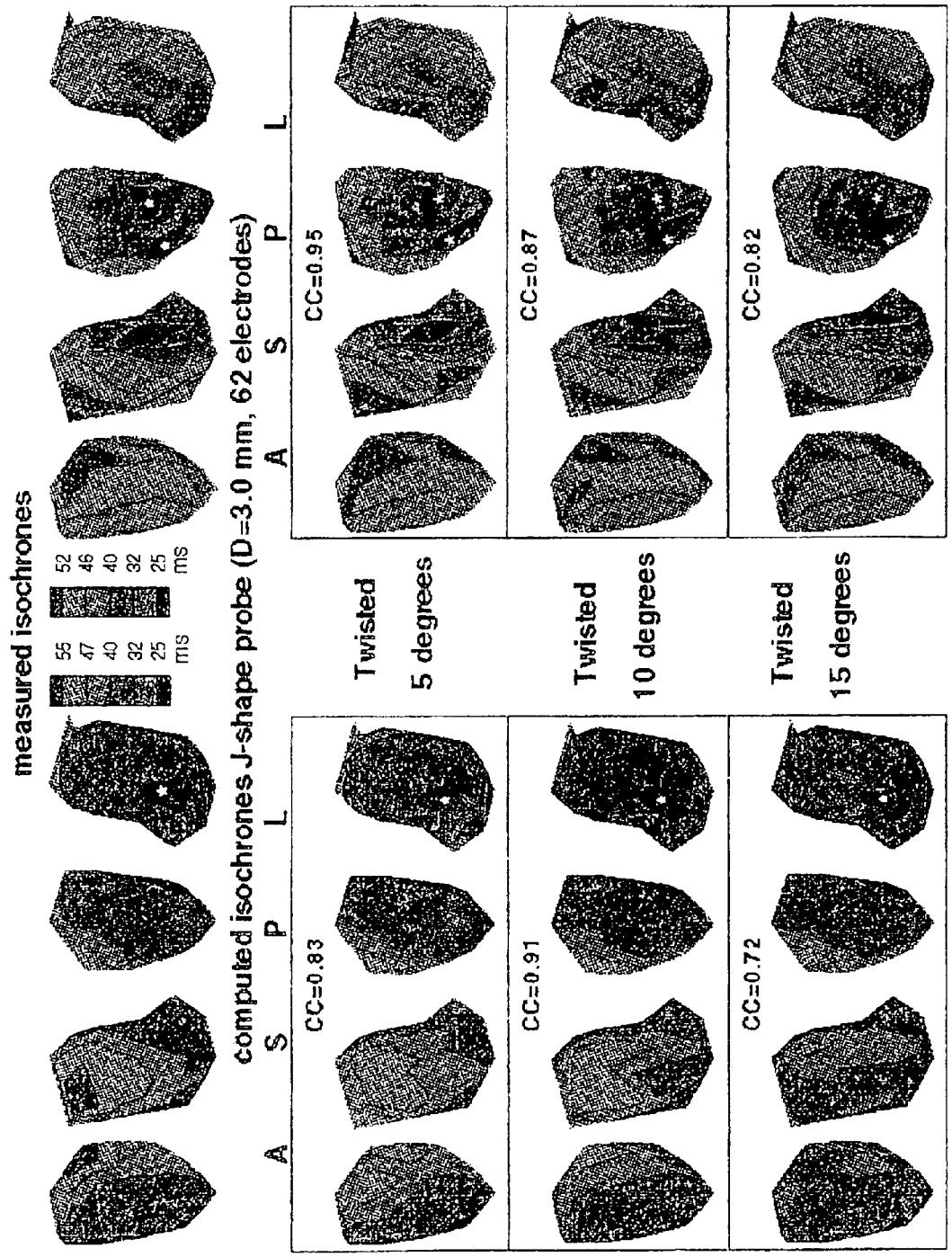
FIG. 23 EFFECTS OF J-PROBE TWIST ON ISOCHRONE MAP

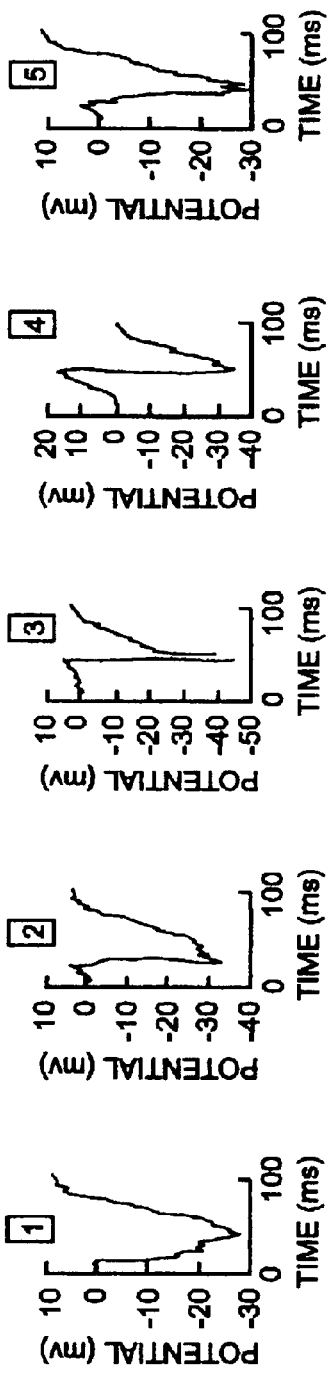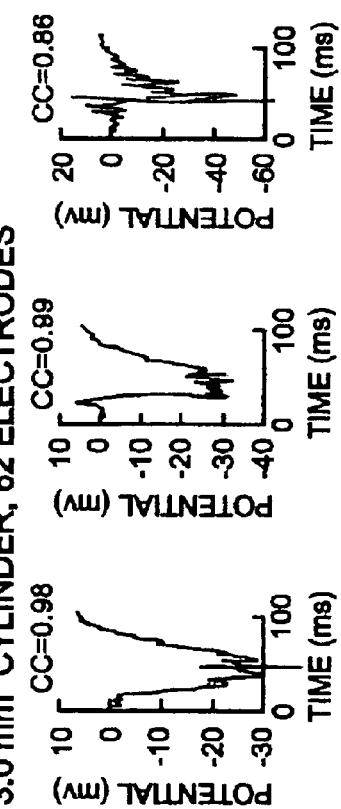
FIG. 24(a)
FIG. 24(b)

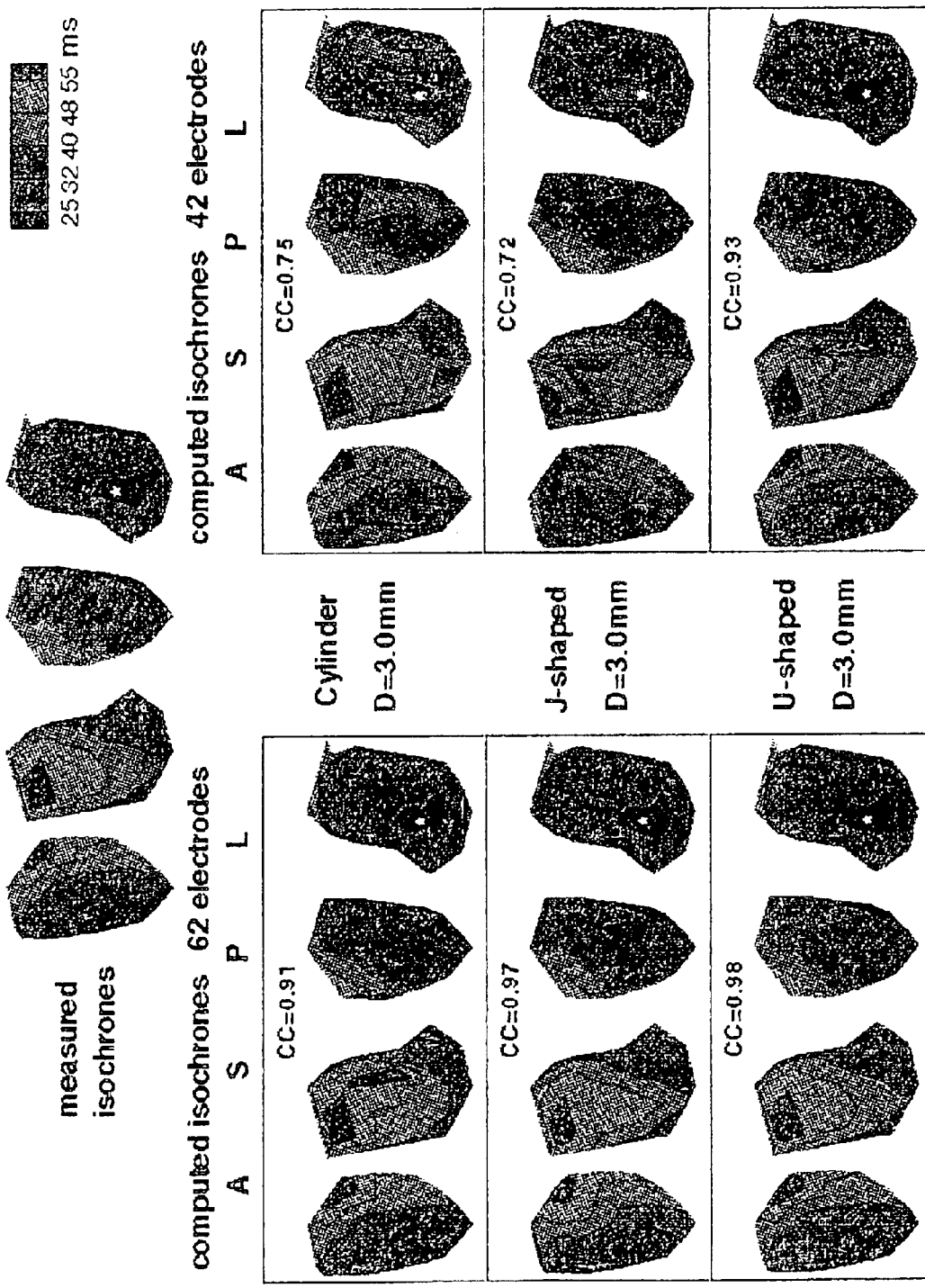
FIG. 25 EFFECTS OF CATHETER SHAPE ON ISOCHRONE MAP

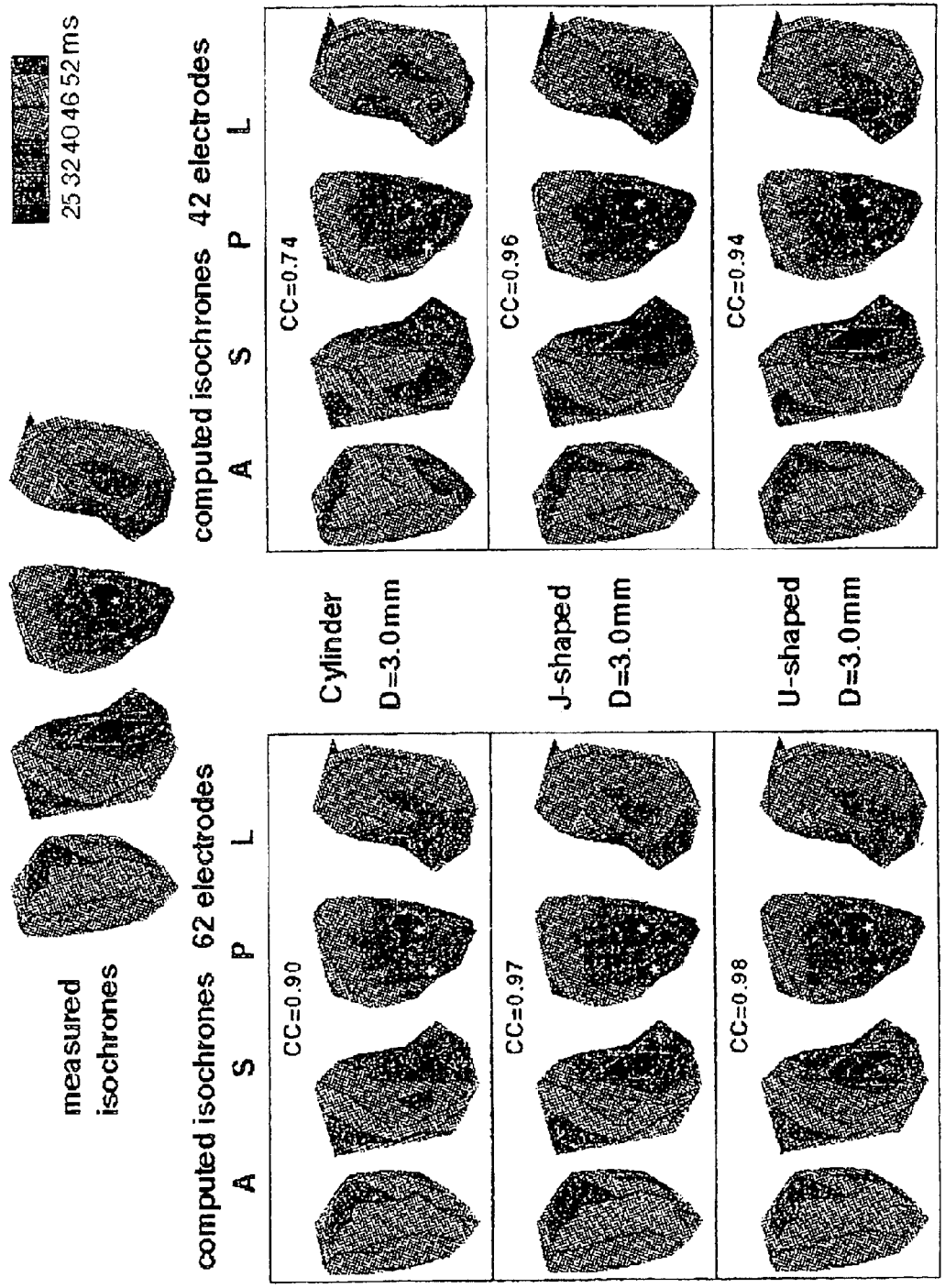
FIG. 26 EFFECTS OF CATHETER SHAPE ON ISOCHRONE MAP

ELECTROPHYSIOLOGICAL CARDIAC MAPPING SYSTEM BASED ON A NON-CONTACT NON-EXPANDABLE MINIATURE MULTI-ELECTRODE CATHETER AND METHOD THEREFOR

This application is a 371 of PCT/US98/15712, Jul. 29, 1998 which claims benefit of provisional application Ser. No. 60/054,342 filed Jul. 31, 1997.

This research is supported by the National Institutes of Health, Grant No. 2 RO1 HL-33343 (Sponsor: NIH-NHLRI).

BACKGROUND OF THE INVENTION

This invention relates to an apparatus and method for electrophysiological cardiac mapping. More particularly, the invention is directed to a system based on a nonexpandable, noncontact, miniature, multielectrode catheter which is used to measure electrical potentials within a heart cavity. These measured potentials are then used, along with data on the geometric relationship between the catheter and the endocardial surface, to reconstruct maps representing endocardial electrical activity. In this regard, electrograms and isochrones are reconstructed.

While the invention is particularly directed to the art of electrophysiological cardiac mapping, and will be thus described with specific reference thereto, it will be appreciated that the invention may have usefulness in other fields and applications.

By way of background, endocardial potential mapping is a tool for studying cardiac excitation and repolarization processes. Mapping endocardial potential distribution and its evolution in time is useful for analyzing activation and repolarization patterns and for locating arrhythmogenic sites and regions of abnormal electrical activity in the heart. Accurate localization of arrhythmogenic sites is important to the success of non-pharmacological interventions, such as catheter ablation.

Unfortunately, current techniques of mapping potentials directly from the endocardium present certain difficulties. For example, the well-known "roving" probe approach is 1) limited in the number of recording sites, 2) too time consuming and 3) only operative to collect data over a plurality of heart beats, instead of a single beat. Therefore, this approach is not useful on a beat-by-beat basis to study dynamic changes in the activation process.

In addition, multiple electrode balloons or sponges have also been used to map electrical activity of the heart by way of measuring potentials within a heart cavity. Although capable of mapping the entire endocardium, these devices occlude the heart cavity and require open heart surgery, heart-lung bypass and other complicated and high risk procedures.

Another device having a multiple-spoke, basket-shaped recording catheter allows simultaneous acquisition of potential data from multiple electrodes without occluding the cavity. However, the basket is nonetheless limited in the number of electrodes so that spatial resolution is relatively low. Moreover, it is difficult to insure that all electrodes make contact with the endocardium. Also, the basket can be entangled in intracavitary structures such as the chordae tendineae. The fact that the basket must be collapsed prior to catheter withdrawal from the ventricle adds complexity and risk to this procedure.

Still another known device for detecting endocardial potentials uses an electrode array catheter that can be expanded within the heart chamber but does not occlude the heart chamber. However, this system still involves undesirable expansion of a device in the heart chamber. The expanded element may interfere with intracavity structures and adds complexity to the system because it must be collapsed before removal. Moreover, it is difficult to determine the location of the electrodes within the chamber. Also, the array may not expand as desired, leading to inaccuracies in mapping.

Taccardi et al. developed an alternative indirect mapping approach that makes use of a large (too large for clinical applications) intracavitary multielectrode catheter-probe (olive shaped or cylindrical), that can be introduced into the blood filled cavity without occluding it. The probe permits simultaneous recording of intracavitary potentials from multiple directions but, unlike the balloon, is not in direct contact with the endocardium and does not record actual endocardial potentials. The intracavitary probe potentials exhibit smoothed-out distributions and do not reflect details of the excitation (or repolarization) process that can be detected and located by direct endocardial recordings. It is highly desirable, therefore, to develop an approach for reconstructing endocardial potentials, electrograms and isochrones from data recorded with a small, non-expanding intracavitary catheter-probe that can be introduced percutaneously, does not occlude the ventricle, and/or does not require opening large structures (e.g. basket or balloon) inside the cavity.

Accordingly, it would be desirable to have available a multielectrode catheter probe that can be introduced percutaneously, without expanding inside the ventricular cavity, and provide accurate reconstructed endocardial potentials, electrograms and isochrones.

The present invention contemplates a new and improved system and method for electrophysiological cardiac mapping using a non-contact, non-expandable catheter which resolves the above referenced difficulties and others and attains the above referenced desired advantages and others.

SUMMARY OF THE INVENTION

A system for determining electrical potentials on an endocardial surface of the heart is provided. In one aspect of the invention, the system contains a noncontact, non-expandable, miniature catheter probe that is percutaneously positioned inside a heart cavity. A plurality of electrodes are disposed on an end portion of the probe whereby electrical potentials within the heart cavity are measured. Also included is a means for generating a matrix of coefficients which is then used along with the electrical catheter potentials to determine endocardial potentials.

In a further aspect of the invention, the probe assumes a curved shape inside the cavity.

In a further aspect of the invention, the system includes means for generating electrograms and isochrones based on the determined endocardial potentials.

In a further aspect of the invention, the curved shape of the terminal end of the electrode catheter resembles a "J", "U", "O", helix, pigtail, or any general curved shape.

In a further aspect of the invention, the system includes a means for conforming the terminal end portion of the probe to the first elongated shape and a means for conforming the terminal end of the end portion of the probe into the second curved shape.

In a further aspect of the invention, a method for implementing the system is provided.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

DESCRIPTION OF THE DRAWINGS

The present invention exists in the construction, arrangement, and combination of various parts of the device and steps of the methods, whereby the objects contemplated are attained as hereinafter more fully set forth, specifically pointed out in the claims, and illustrated in the accompanying drawings in which:

FIGS. 4(a)–(e) are side views of the end portion of various catheter probes according to the present invention having another second shape;

FIG. 12 includes isochrone maps showing results obtained using the present invention;

FIG. 13 includes isochrone maps showing results obtained using the present invention;

FIG. 16 includes isochrone maps showing the effects of probe rotation of 5/ on the present invention;

FIG. 17 includes isochrone maps showing the effects of probe rotation of 10/ on the present invention;

FIG. 18 includes isochrone maps showing the effects of probe rotation of 5/ and 10/ on the present invention;

FIG. 20 includes isochrone maps showing the effects of probe shift on the present invention;

FIG. 21 includes isochrone maps showing the effects of probe shift on the present invention;

FIG. 23 includes isochrone maps showing the effects of twisting on the present invention;

FIG. 25 includes isochrone maps showing the effects of catheter shape on the present invention;

FIG. 26 includes isochrone maps showing the effects of catheter shape on the present invention;

DETAILED DESCRIPTION OF THE PREFERRED EMBODIMENTS

Figure 1A:
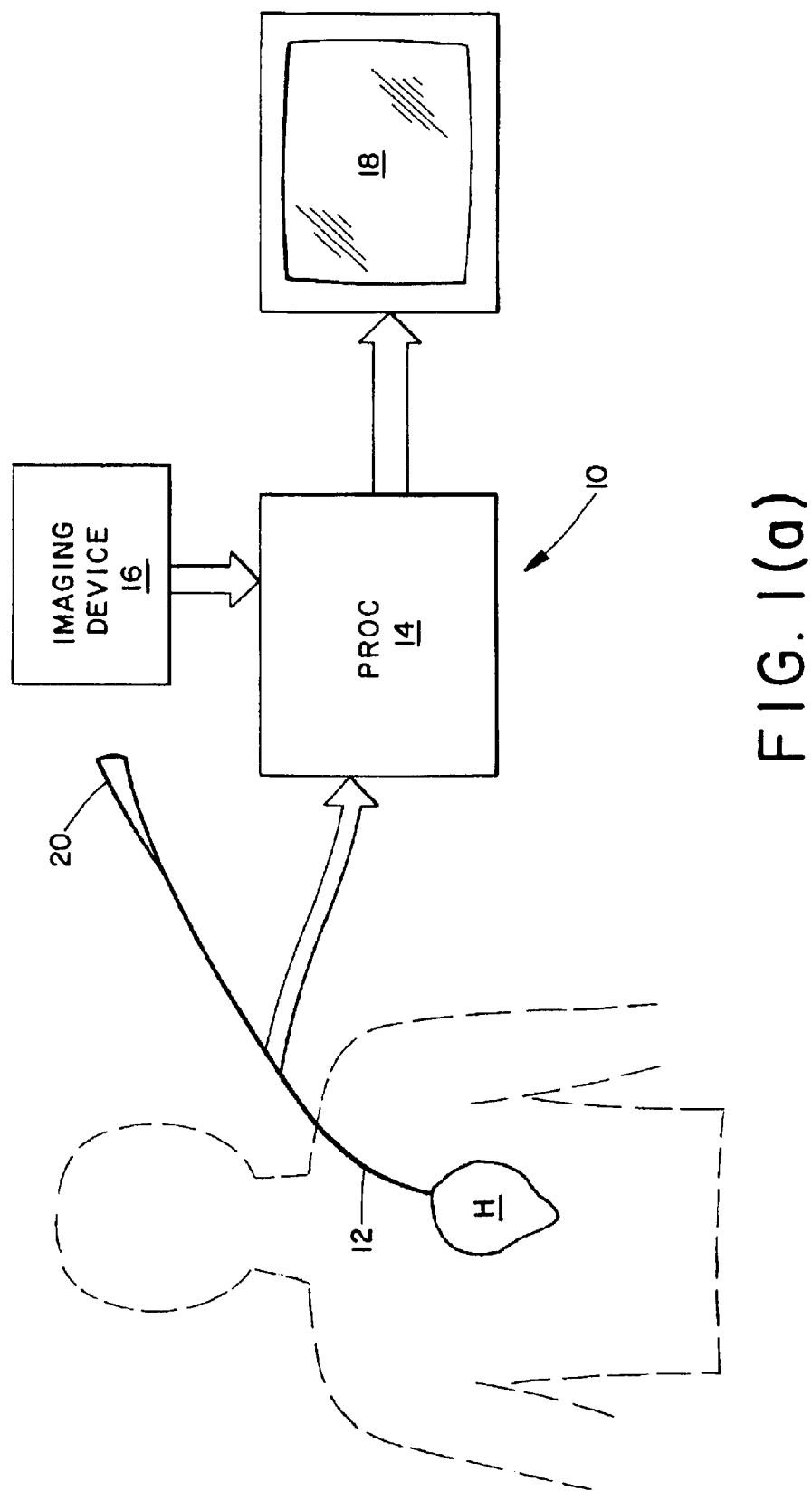
FIG. 1(a) is a representative illustration of the system according to the present invention.

A mathematical inverse methodology for reconstruction of endocardial potentials, electrograms and isochrones from non-contact, intracavitary probe measurements has been developed and validated. A study in an isolated canine left ventricle (LV) demonstrated that the inversely computed endocardial potential maps reconstruct with good accuracy and resolve the major features of the measured endocardial potential maps, including maxima, minima and regions of negative and positive potentials. A more recent systematic evaluation demonstrated that computed temporal electrograms and isochrones also closely approximate their directly measured counterparts. The isochronal maps correctly captured the regions of early and late activation for a single pacing site and for two simultaneous pacing sites separated by 17 mm. Moreover, the entire activation sequence was closely approximated, including regions of nonuniform conduction (e.g. isochrone crowding indicating slow conduction). The size of the probe, though, was too large for clinical application.

The reconstruction methodology can be adapted to the clinical environment with two additional developments: (1) reduction in size of the intracavity multielectrode probe; and (2) noninvasive determination of the geometric relationship between the probe and the endocardium. A 9-French (3-mm) multielectrode catheter that can be introduced percutaneously has been developed. The present invention demonstrates that endocardial potentials can be reconstructed from a 3-mm cylindrical probe with accuracy.

In the experiments (the results of which are outlined herein with reference to FIGS. 8–30), the geometry of the endocardium was determined invasively after completion of the potential measurements. The ability to measure the geometry directly improved accuracy. However, the fact that the geometry was not obtained at the time of potential measurements introduced an error, since myocardial changes upon termination of perfusion changed somewhat the positions of the intramural needles. Moreover, all computations assumed a single cavity geometry (end-diastolic volume) throughout the experiment, whereas the degree of blood filling varied between pacing protocols and between time frames during a given protocol. The probe positions/orientation within the cavity was estimated using an automated optimization procedure and was subject to error as well.

Nonetheless, the experiments confirm that, in spite of geometry errors, electrograms and isochrones can be reconstructed over the entire endocardium with good accuracy. This property is useful in terms of clinical application of the approach.

As will be described below, existing noninvasive imaging techniques, such as ultrasound, can provide the endocardial geometry and probe position simultaneously and at the time of potential measurements. This constitutes an improvement over the method used in the experiments. The geometric robustness of the reconstruction procedure implies that it could be combined with a noninvasive imaging modality (high accuracy can be achieved with transesophageal echocardiography for example) to reconstruct endocardial potentials, electrograms, and isochrones on a beat-by-beat basis in the clinical catheterization laboratory.

Figure 1B:
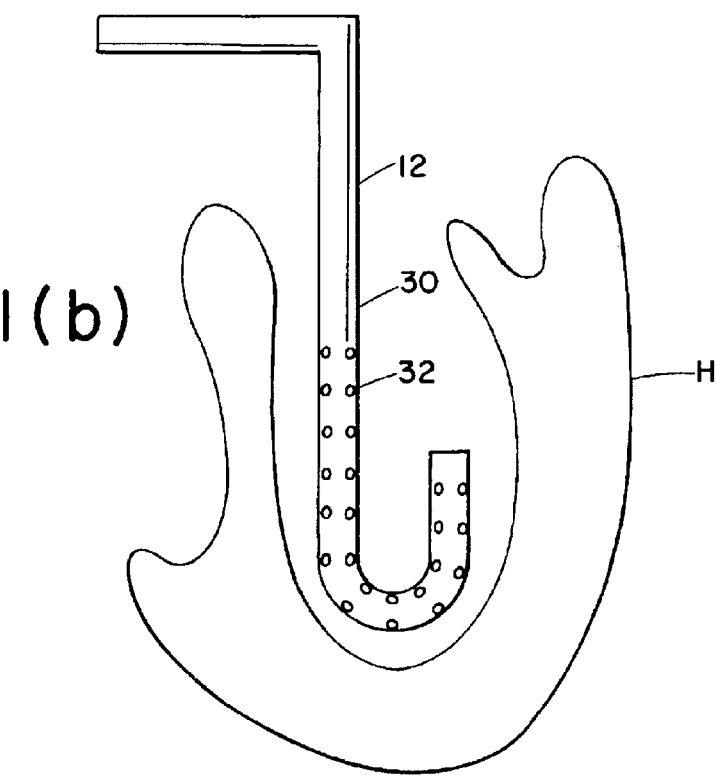
FIG. 1(b) is an illustration of the catheter according to the present invention positioned within a heart cavity.

Referring now to the drawings wherein the showings are for purposes of illustrating the preferred embodiments of the invention only and not for purposes of limiting same, FIG. 1(a) provides a view of the overall preferred embodiment. As shown, the system 10 includes a catheter probe 12—which is positioned in a cavity of the heart H by well known methods—a processor (or computer) 14, an imaging (or geometry determining) device 16, an output device 18 (which may take the form of a display (as shown), or a printer or other suitable output device), and a mechanism 20 for steering and manipulating an end portion of catheter probe 12. FIG. 1(b) shows the catheter 12 (shown in an exemplary curved shape) positioned in the heart H.

Figure 2:
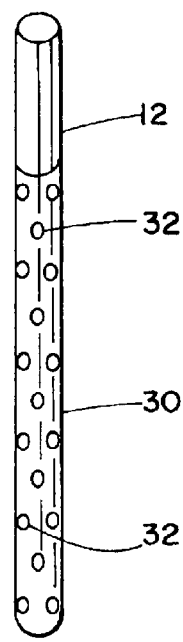
FIG. 2 is a side view of an end portion of a catheter probe according to the present invention having a first shape.

The end portion 30 of catheter probe 12, as shown in FIG. 2, is generally cylindrical in cross section and has disposed thereon a plurality of electrodes, exemplary shown at 32. It should be noted that herein, like numerals in the drawings indicate like elements. Preferably, the catheter probe is a 9-French (9F), 3.0 mm catheter; however, any usable style and size will suffice. For clinical applications, of course, the catheter is preferably of a size to facilitate percutaneous introduction into the cavity. The number of electrodes may vary depending on the needs of the particular application. Of course, varying the number of electrodes consequently impacts the results obtained using the invention, as will be more particularly described hereinafter.

Figure 3:
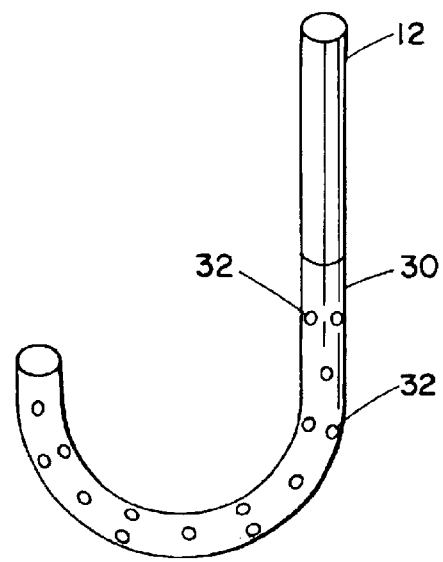
FIG. 3 is a side view of the end portion of the catheter probe according to the present invention having a second shape.

As illustrated in FIG. 3, the end portion of the catheter probe 12 may be conformed to a curved shape of FIG. 3 once positioned in the heart cavity. As shown, the exemplary shape is that of a "J". It should be emphasized that the label "J" (and other similar labels) refers to the end portion of the catheter that has electrodes disposed thereon, not the entire catheter. The end portion is conformed to this shape by known methods and the mechanism 20 represented generally in FIG. 1, as those skilled in the art will appreciate.

Figure 4A:
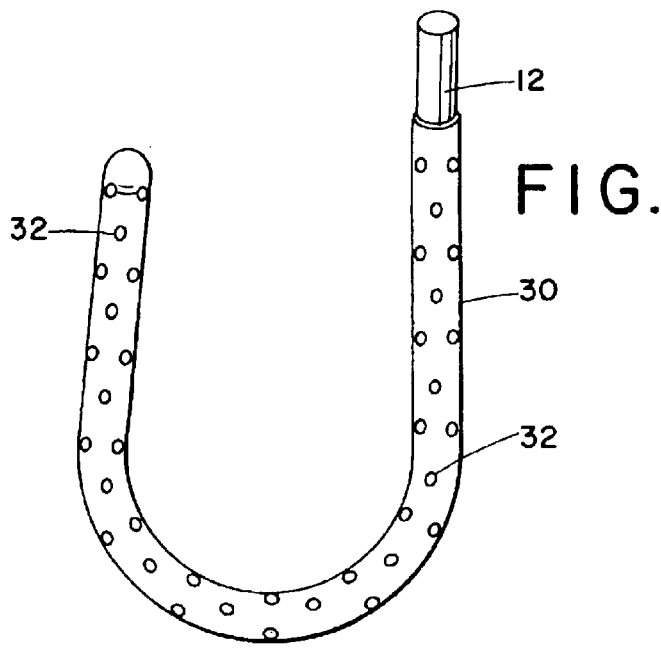
Figure 4B:
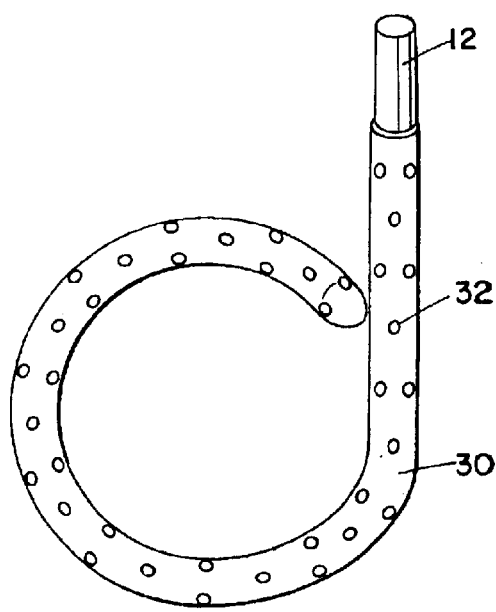
Figure 4C:
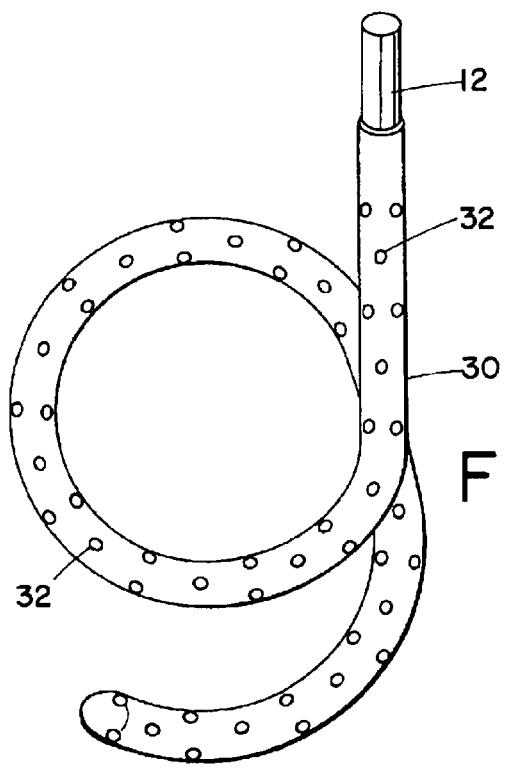

Of course, the precise shape of the end portion 30 of the catheter probe 12 may be varied to suit a particular application of the catheter probe. For example, the end may be conformed to a "U," "O", pigtail, helix or any known curve. As is shown in FIG. 4(a), the exemplary "U" shaped catheter end portion shape is shown whereby the end portion is further manipulated from the J-shape to resemble a "U". The angle of curvature is preferably the same as that of the J-shaped configuration but it is recognized that the angle of curvature may be varied without affecting the scope of the invention. FIGS. 4(b)–(e) show curved catheters having end portions conformed to an "O", a pigtail, a helix, and a general representative curve, respectively. It should be appreciated that varying the shape of the end portion of the catheter probe impacts the results obtained using the invention, as will be more particularly described hereinafter but, importantly, the invention and resultant test data indicate that a noncontact, nonexpandable, miniature multielectrode catheter probe of any shape or configuration (including straight) is useful for cardiac mapping.

Figure 5A:
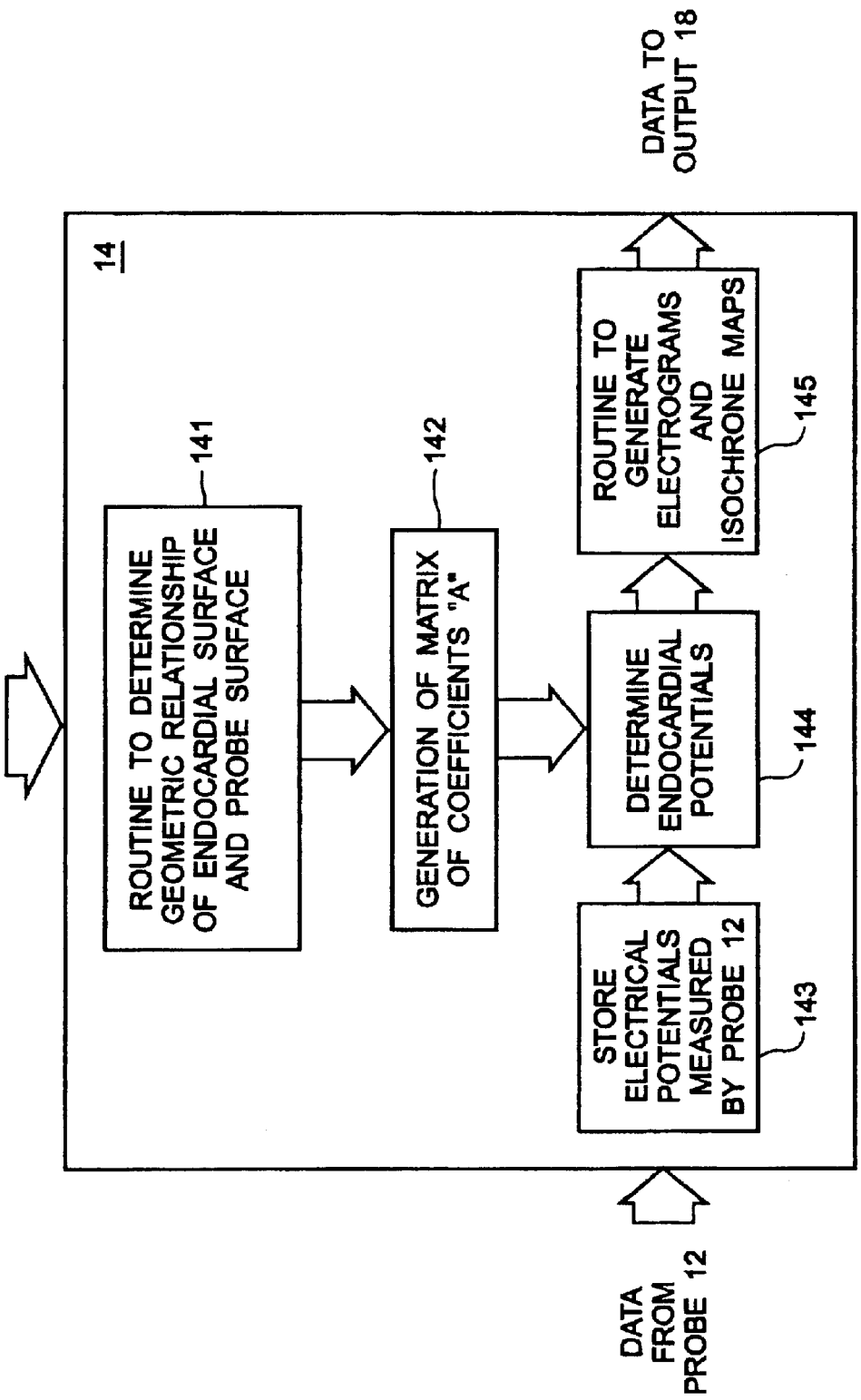
FIG. 5(a) is a functional block diagram of the processor according to the present invention.

Referring now to FIG. 5(a), functional blocks of the processor 14 are described. Those skilled in the art will appreciate that the processor 14 actually includes suitable software and hardware (including, for example, memories) that accomplish the functions described. In one embodiment, the software tool implemented takes the general form of that described in connection with FIG. 5(b), although neither the processor nor the tool is so limited. For example, it should be recognized that the software tool of FIG. 5(b) has features involving testing and validation which are not specifically described in connection with FIG. 5(a) but would be apparent to those of skill in the art.

Specifically, as shown in FIG. 5(a), data on geometry of the endocardium and probe are input to the processor 14 from the imaging device 16. Such data may be generated using existing imaging modalities such as x-ray, ultrasound, computed tomography (CT), magnetic resonance imaging (MRI), . . . etc. Preferably, the invention is implemented using bi-plane x-ray techniques enhanced with fluoroscopy. These techniques result in determination of a geometric envelope that approximates the heart chamber.

As is shown in FIG. 5(a), at least one of these known imaging routines is available to provide data to determine a geometric relationship of the endocardial surface (or envelope) and probe surface (block 141) based on the input of the imaging device 16. A matrix of coefficients A, described in more detail below, is also generated (block 142) in the processor. In addition, data, i.e. electrical potentials measured in the heart cavity, is input to the processor from the probe 12. These data are stored in the processor (block 143). Endocardial potentials may then be determined by the processor based on the stored electrical potentials and the matrix of coefficients (block 144). Electrograms and isochrone maps are also generated for display and evaluation (block 145). The results, of course, may be output.

Figure 5B:
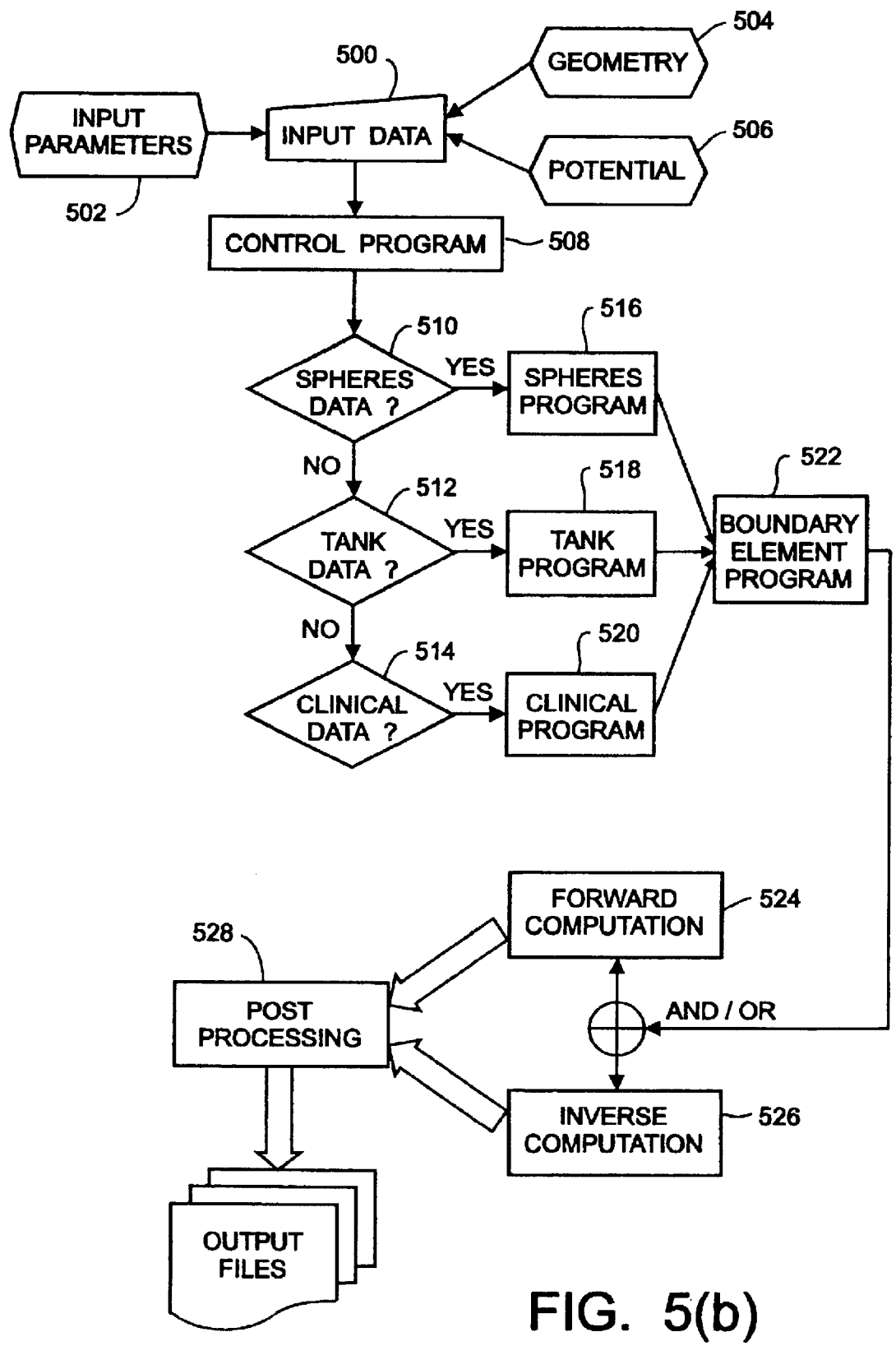
FIG. 5(b) is a flow diagram illustrating a software tool implemented according to the present invention.

As noted above, the software tool may take the general form of the flow diagram illustrated in FIG. 5(b), but those skilled in the art will appreciate that such a program, which (as will be described) also accommodates testing and validation processes, may well be modified and/or evolve into a modified tool (to resemble, for example, only the features described in connection with FIG. 5(a)) as the present invention is modified as a result of additional development or needs of users. Those skilled in the art will also appreciate that the description of this software tool necessarily overlaps with the description in connection with FIG. 5(a) because the processor of FIG. 5(a) implements such software tools in the described embodiment.

As shown, information is input to the system (step 500). Specifically, parameters are input to the system by the user (step 502). Geometry data and potential data are also input (steps 504, 506). It should be recognized that in a clinical setting, the geometry data is generated by imaging device 16 and potential data is generated by catheter probe 12; however, if the software tool is implemented for testing and validation purposes, the geometry data may be known parameters, such as those associated with geometric spheres and torso tanks (used in testing), that are simply input to the system. The overall control program is implemented (step 508) and it is determined whether to use the software tool for testing and validation (using sphere or torso tank data (steps 510, 512)) or clinical application (using clinical data (step 514)). Appropriate processing is then conducted on the data (steps 516, 518 or 520), as will be apparent to those skilled in the art, to prepare the data for necessary mathematical manipulation.

Next, a boundary element method (further described below) is applied (step 522). At that time, forward (step 524) or inverse (step 526) computations, as necessary, are performed. Of course, for clinical applications, only inverse computations (as described below) are used. Once the data is computed, processing of the data for output is accomplished (step 528).

Figure 6:
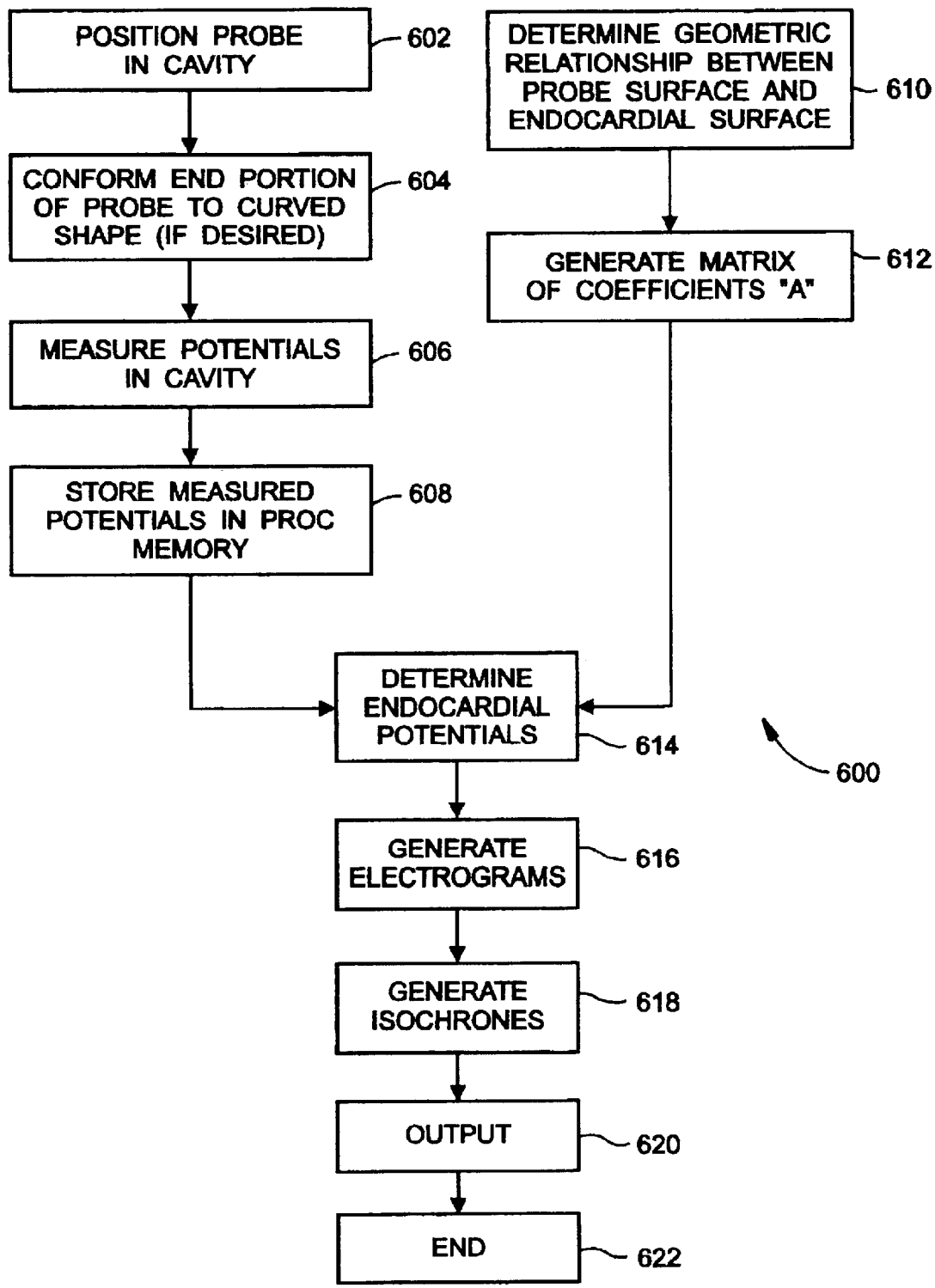
FIG. 6 is a flow chart showing the method according to the present invention.

Referring now to FIG. 6, the overall method 600 by which endocardial potentials (and electrograms and isochrones) may be determined according to the present invention is described. Initially, a probe 12 is percutaneously positioned in the cavity of a heart by known methods (step 602). If desired, the end portion of the probe is then conformed, utilizing mechanism 20, to a curved shape such as those shown in FIGS. 3 and 4(*a*)–(*e*) (step 604). It is recognized that conforming the end portion may not be necessary if the results obtained by using the straight catheter (of FIG. 2, for example) are acceptable. Potentials are then measured in the cavity (step 606) and stored (step 608).

A geometric relationship between the probe surface and the endocardial surface (or envelope) is also determined (step 610). The geometry is, of course, determined using the imaging device 16. Based on this data on the geometric relationship, a matrix of coefficients A is generated (step 612).

Next, endocardial potentials are determined based on the stored potentials and the matrix of coefficients (step 614). Electrograms and isochrones are then generated by the processor (steps 616 and 618) and displayed (step 620). The procedure is then ended (step 622).

The mathematical computations accomplished by the processor 14 involved in implementing the present invention described above relate to and should be analyzed by considering "forward" computations, i.e. calculating catheter probe potentials from known endocardial surface potentials, and "inverse" computations, i.e. calculating endocardial surface potentials based on measured probe potentials. Of course, the inverse computation is the computation that is used for implementation of the present invention (e.g. step 614 in FIG. 6), but understanding the forward computation is also useful.

Figure 7:
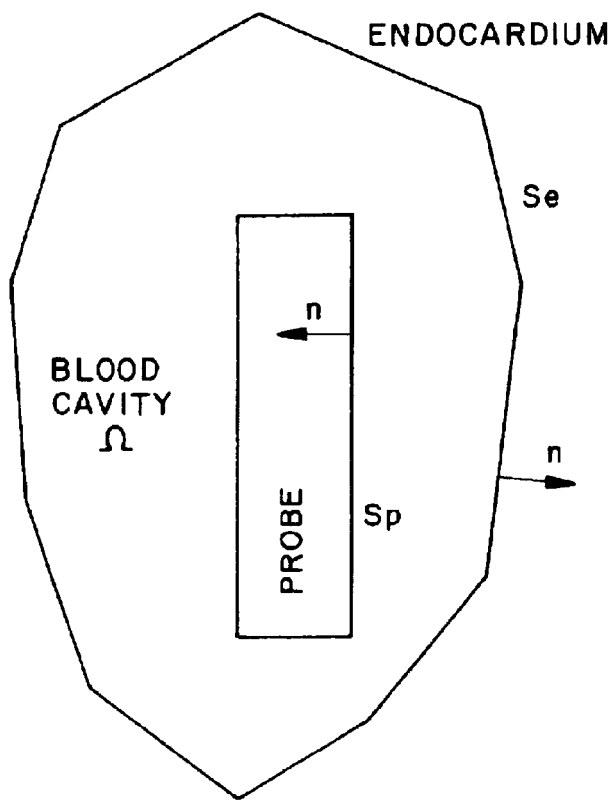
FIG. 7 is a schematic representing the geometry of a human ventricular cavity containing a probe.

While various forward and inverse computations are known, the computations involved in connection with the present invention are as follows. More particularly, computation of probe potentials based on measured endocardial potentials (the "Forward Problem") requires solving Laplace's equation in the cavity volume ($\Omega$) bounded by the probe surface ($S_p$) and the endocardial surface ($S_e$), as illustrated in FIG. 7.

Below is a description of the mathematical formulation. Further details can be found in previous publications such as Khoury D S, B. Taccardi, Lux R L, Ershler P R, Rudy Y, "Reconstruction of endocardial potentials and activation sequences from intracavitary probe measurements," *Circulation*, 91:845–863 (1995); Rudy Y, Messinger-Rapport B J, "The inverse problem in electrocardiography solutions in terms of epicardial potentials," *CRC Crit Rev Biomed Eng.*, 16:215–268 (1988); Rudy Y, Oster H S, "The electrocardiographic inverse problem," *CRC Crit Rev Biomed Eng.*, 20:25–46 (1992), Messinger Rapport B J, Rudy Y, "Computational issues of importance to the inverse recovery of epicardial potentials in a realistic heart-torso geometry," *Math Biosci*, 97:85–120 (1989) (published erratum in *Math Biosci*, 99(1):141 (1990 April)); Oster H S, Rudy Y, "The use of temporal information in the regularization of the inverse problem of a electrocardiography," *IEEE Trans Biomed Eng.*, 39:65–75 (1992); and Messinger Rapport B J, Rudy Y, "Regularization of the inverse problem in electrocardiography. A model study," *Math Biosci*, 89:79–118 (1988), all of which are hereby incorporated herein by this reference.

The behavior of potential, V, within $\Omega$ is governed by Laplace's equation:

$$\Delta^2 \underline{V} = 0 \text{ in } \Omega \tag{1}$$

subject to the boundary conditions:

$$\underline{V} = \underline{V}_P \text{ on a subset of } S_p \tag{2}$$

$$\partial V/\partial n = 0 \text{ on } S_p \tag{3}$$

where $V_p$ is the potential on the probe surface; $\partial V/\partial n = 0$ implies that current cannot enter the nonconducting probe. A well-known Boundary Element Method (BEM) (See, for example, Brebbia C A, Dominguez J, *Boundary elements: An Introductory Course*, McGraw-Hill Book Co., New York (1989) or Brebbia et al., *Boundary Element Techniques. Theory and Applications in Engineering*, Springer Verlag, Berlin (1984)) is used to numerically solve for the potentials in a realistic geometry cavity-probe system. This results in the following equation that relates the probe potentials to the endocardial potentials:

$$V_p = A \cdot V_e \tag{4}$$

where $V_p$ is a vector of probe potentials of order $N_p$ (probe surface nodes), $V_e$ is a vector of endocardial potentials of order $N_e$ (endocardial surface nodes), and A is an $N_p \times N_e$ matrix of influence coefficients determined by the geometric relationship between the probe surface and the endocardial surface. The intracavitary probe potentials can be calculated from the endocardial potentials using equation (4). Since the forward computation is a stable and accurate process, the computed probe potentials provide an accurate estimate of cavity potentials measured by an actual probe of the same design and in the same intracavitary position. This calculation is useful to verify data that are obtained using the inverse computation.

The matrix A in equation (4) is determined by the geometrical relationship between the endocardial surface and the probe surface. Specifically, it requires specification of node positions (corresponding to electrode positions) on the probe and node positions on the endocardium. Geometry data, as noted above, is obtained from the imaging device 16 which, again, may involve any of the known imaging modalities. Errors in determining the node positions on these two surfaces, especially probe electrodes, may be amplified due to the nature of the inverse procedure and might consequently introduce errors in the reconstructed endocardial potentials. Accordingly, accurate determination of geometry is important for implementation.

In order to compute endocardial electrograms and isochrones, endocardial potential maps are first computed in a quasi-static fashion for every millisecond throughout the endocardial activation process. Computing endocardial potentials is the first step in computing temporal electrograms and isochrones. To compute endocardial potentials from probe potentials, the relationship between $V_e$ and $V_p$ established in equation (4) must be inverted. However, because of the ill-posed nature of the problem (as described in Rudy Y, Messinger-Rapport B J, "The inverse problem in electrocardiography: solutions in terms of epicardial potentials," *CRC Crit Rev Biomed Eng.*, 16:215–268 (1988)), one cannot simply invert matrix A to obtain the endocardial potentials ($V_e$) from probe potentials ($V_p$). A Tikhonov regularization technique is used to stabilize the procedure (See, for example, Tikhonov A N, Arsenin V Y, "Solution of Ill-Posed Problems," 27–94, V H Winston & Sons, Washington, D.C. (1977), or Tikhonov et al., "Solutions of ill-posed problems," (trans. from Russian) Wiley, N.Y. (1977), which are incorporated herein by reference), and the solution for endocardial potentials is obtained by minimizing the objective function:

$$\min/v_e[||V_p - A \cdot V_e||^2 + t||V_e||^2] \quad (5)$$

or, more generally, minimizing $$||V_p - A \cdot V_e||^2 + tF[V_e]$$

where t is a regularization parameter, whose optimal value was determined using the CRESO (composite residual and smoothing operator) method (See, Colli-Franzone P, Guerri L, Taccardi B. Viganotti C, "Finite element approximation of regularized solutions of the inverse potential problem of electrocardiography and applications to experimental data" Calcolo 1985, 22:91–186, and Colli-Franzone et al., "Mathematical procedure for solving the inverse problem of electrocardiography," *Math Biosci*, 77:353–96 (1985), which are incorporated herein by reference).

The approach to verifying the accuracy of the data obtained is based on a combination of experimentally measured endocardial potentials and simulated catheter probes in an isolated LV preparation. The simulated catheter data is used to reconstruct endocardial electrograms and isochrones, which are then evaluated by direct comparison with their measured counterparts.

In contrast to potentials, electrograms and isochrones provide complete spatio-temporal information for the entire activation cycle. Endocardial electrograms provide temporal information on activation in localized areas and are widely used in clinical practice. Isochrones provide extensive spatio-temporal information about the entire activation sequence that can be seen in one glance. Isochronal maps also can identify spatial nonuniformities of propagation such as regions of slow conduction or areas of conduction block that are important mechanistic properties of arrhythmogenic activity. Therefore, it is useful to evaluate the accuracy with which electrograms and isochrones can be reconstructed from the noncontact catheter. Single-site pacing protocols as well as simultaneous dual-site pacing were employed. Because electrograms and isochronal maps contain temporal information from the entire cardiac cycle, their accurate reconstruction places more demanding design criteria on the catheter probe. The results below demonstrate that, as in the case of potential reconstruction, endocardial electrograms and isochrones can be accurately reconstructed from a noncontact, nonexpandable, miniature multielectrode 9F catheter that may, if desired, assume a curved geometry inside the cavity, without the need for expansion. The catheter need not be curved to work effectively. Curvature simply enhances the results, as will be demonstrated. The reconstruction is robust in the presence of errors, indicating feasibility of the approach in the clinical environment of the electrophysiology (EP) catheterization laboratory.

To obtain an accurate estimate of probe potentials, the forward computation of probe potentials from the measured endocardial potentials was performed with a very large number of "electrodes" (nodes) on the probe surface. In the simulation, probes with 722 electrodes (30 circumferential rows×24 electrodes/row+two end electrodes) were used. This is several times greater than the actual number of electrodes on the probe used in the experiments. As confirmed by spherical model simulations, such a large number of electrodes (nodes) results in very accurate probe potentials. To study the effect of limited electrode density on the reconstruction, different subsets of electrodes (nodes) were selected on the surface of the simulated probe. The uniform spatial distribution of electrodes over the probe surface was preserved. The selected subset of probe potentials was then used in the inverse reconstruction of endocardial potentials. This process was performed for probes of different sizes and shapes.

The reconstruction of endocardial potential maps is performed in a quasi-static approach throughout the cardiac cycle, i.e., at a given time instant, the endocardial map is computed from the probe potentials recorded at the same time. Once all endocardial potential maps are reconstructed, the data are reorganized according to electrode (node) and temporal electrograms depicting potential vs. time can be reconstructed for any position on the endocardial surface. In this study, endocardial potentials and electrograms were computed for 50 positions, where the tip electrodes of endocardial recording needles were located, allowing a direct comparison of the computed electrograms with the actual measured electrograms.

Endocardial isochrones, depicting the activation sequence of the endocardial surface, were constructed from the computed endocardial electrograms. The time derivatives, dV/dt, of the inversely reconstructed endocardial electrograms were computed, and the time instant associated with the maximum negative dV/dt ("intrinsic deflection") at a particular site was taken as the activation time of that site.

Figure 8:
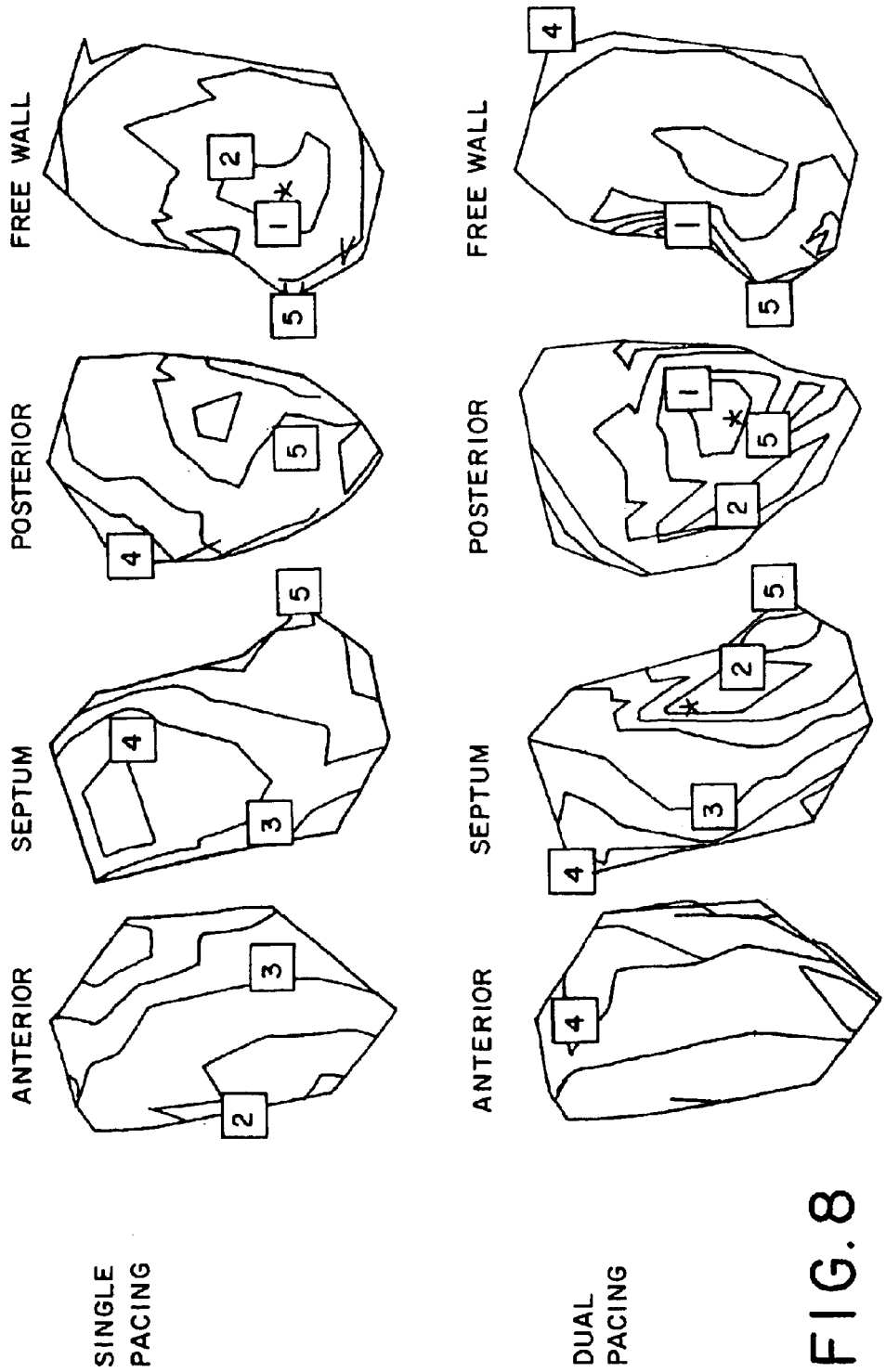
FIG. 8 shows selected sites on the endocardial surface for electrogram display in utilizing the present invention.

Over the entire endocardial surface, 50 electrograms were computed. Electrograms at 5 selected sites are shown in the results. FIG. 8 shows the positions of these selected (numbered) sites. For both single and dual pacing cases, site 1 was chosen to be the earliest (one of the earliest, in the dual pacing case) measured endocardial activation site, while sites 2 to 4 are activated progressively later in time. Site 5 corresponds to a site that is remote from the center of the cavity and therefore far away from the catheter probe. The asterisks correspond to pacing sites.

In the following description of experimental results, three representative simulated catheter probes are compared in terms of accuracy of reconstructed endocardial electrograms and isochrones. The probes are: a cylindrical 7.6 mm diameter probe (generally too large for percutaneous application), a cylindrical 3.0 mm diameter probe (equivalent to a 9F catheter that can be introduced percutaneously), and a 3.0 mm diameter probe bent in the cavity into a J-shape (close to the natural shape assumed by a catheter in the cavity). Results with simulated probes larger than the 7.6 mm cylindrical probe are very similar to those of the 7.6 mm probe. Initial results for a simulated U-shaped catheter probe are also shown to demonstrate the effects of different curved catheter shapes on the reconstructions.

Figure 29:
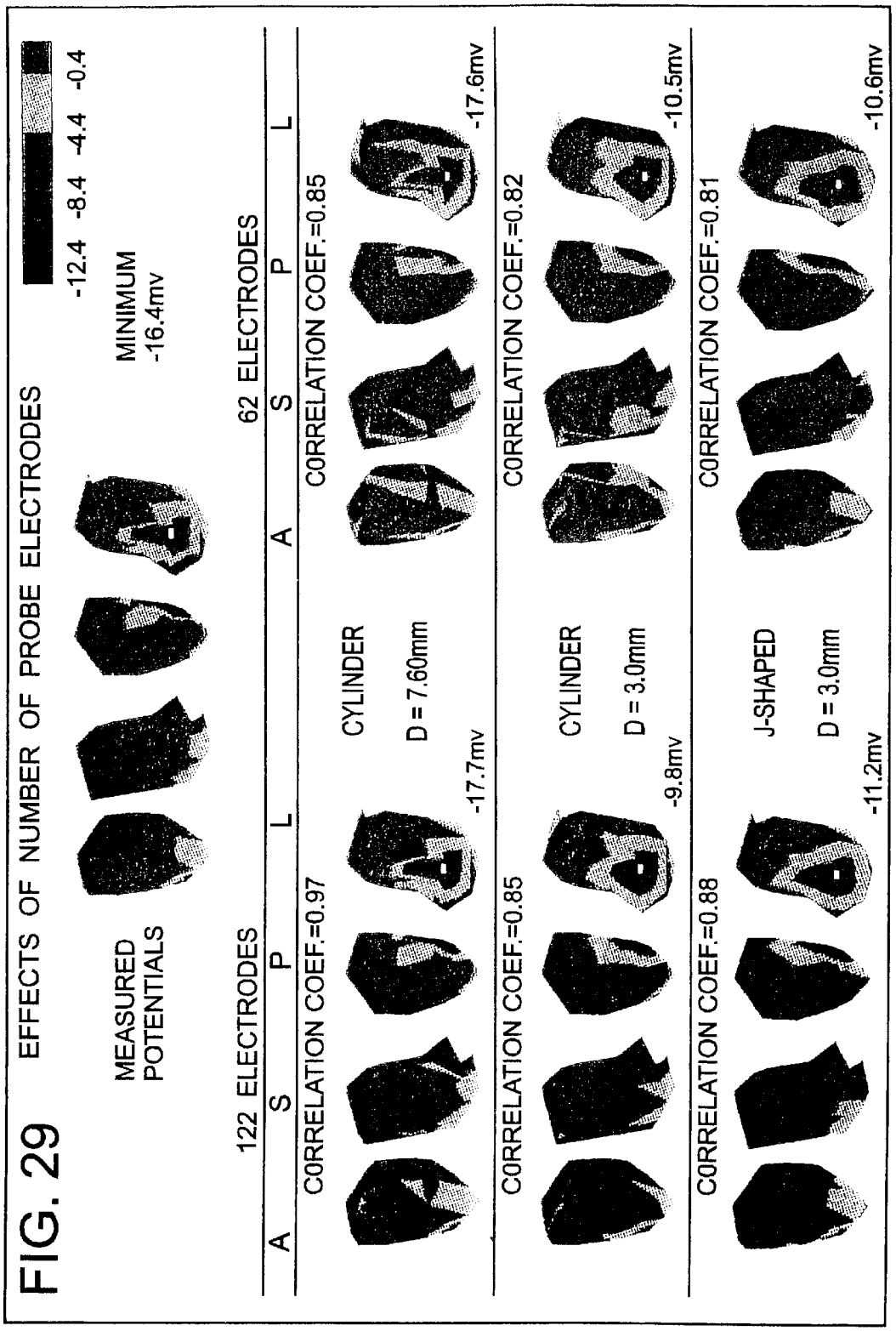
FIG. 29 includes measured and computed potential maps.
Figure 30:
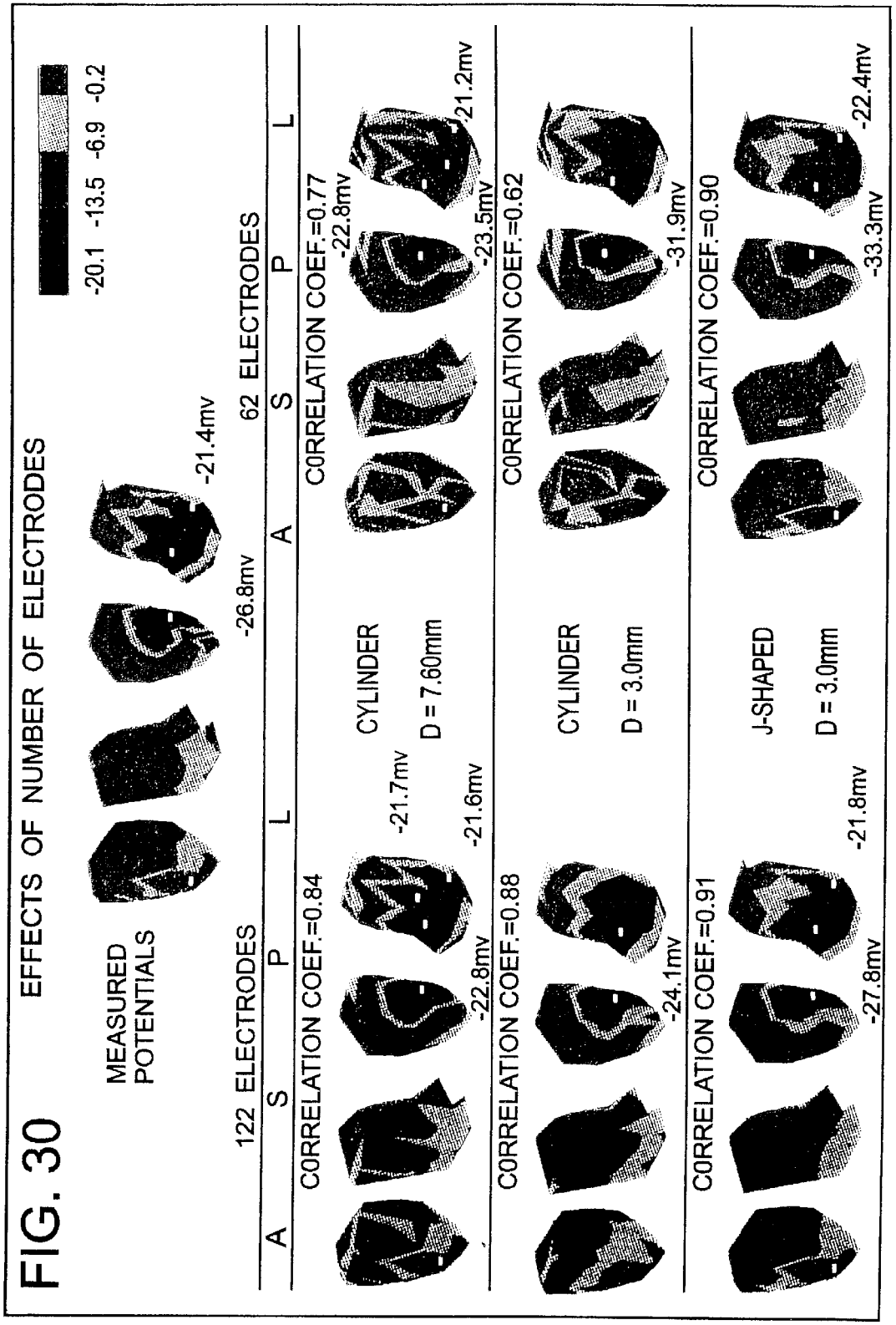
FIG. 30 includes measured and computed potential maps.

It should also be recognized that potential maps may also be generated using the system and method of the present invention. For example, FIG. 29 shows measured and computed potentials for a single pacing site using 122 and 62 electrodes, respectively, for the noted catheters. FIG. 30 shows similar data for dual pacing sites.

Figure 9A:
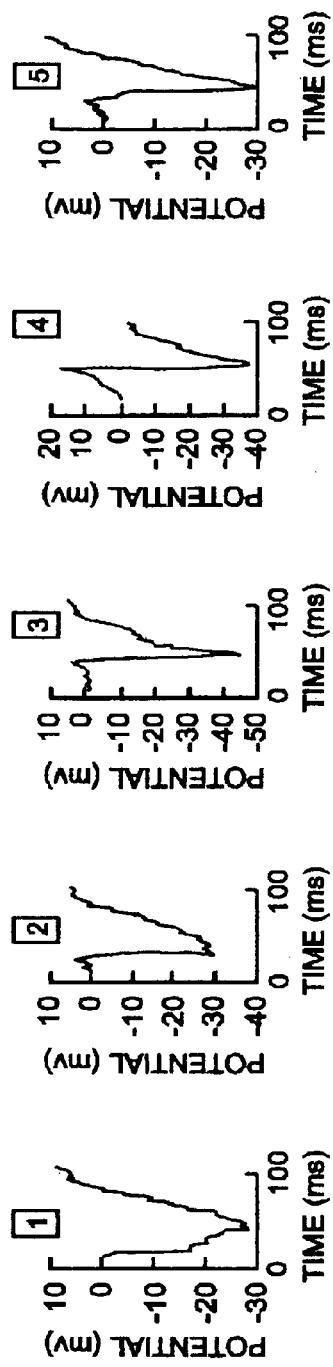
FIG. 9 includes electrograms showing results obtained using the present invention.
Figure 9B:
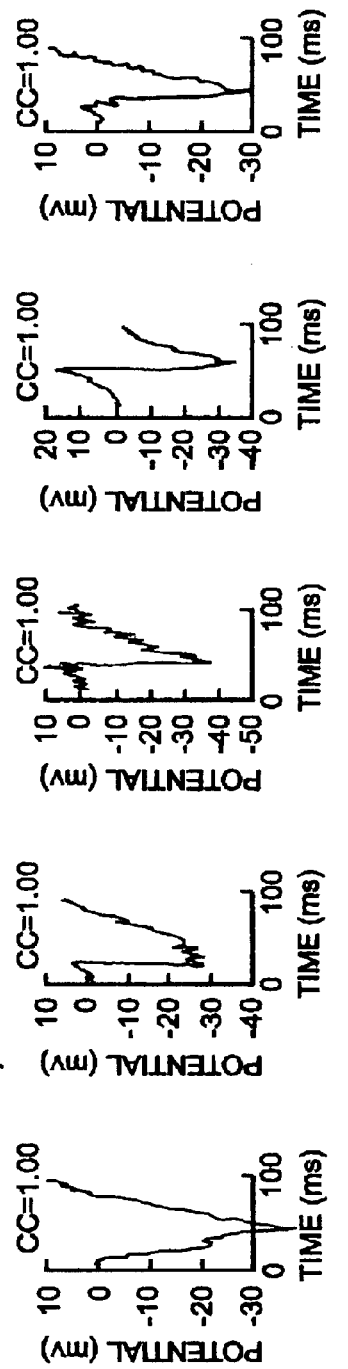

FIG. 9 shows the reconstruction of endocardial electrograms from different probes containing 122 electrodes. The activation sequence is initiated by pacing from a single site.

Measured endocardial electrograms at 5 selected sites are shown at the top, reconstructed electrograms at corresponding sites are shown at the bottom. The correlation coefficients (CC) between the measured and computed electrograms are printed next to each computed electrogram. Over the entire endocardium, computed electrograms at 50 endocardial sites resemble the measured electrograms very well. CC values at all sites are near 1.0.

Figure 10C:
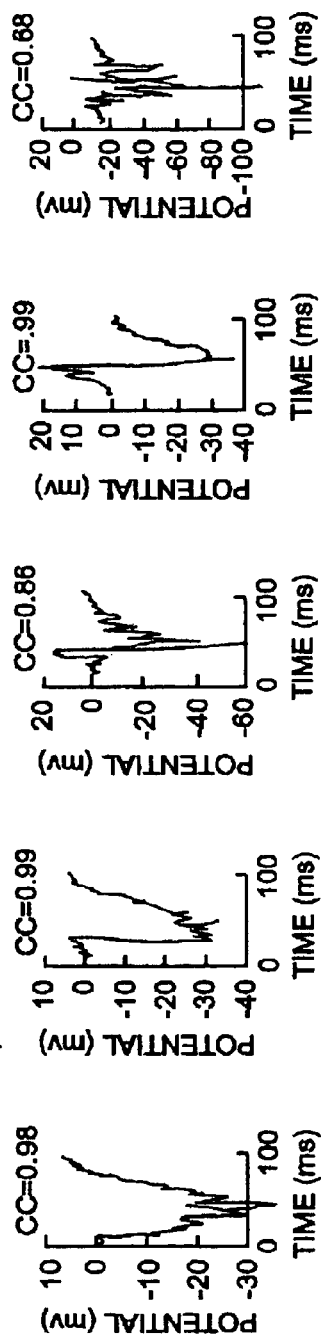
FIG. 10 includes electrograms showing results obtained using the present invention.
Figure 10D:
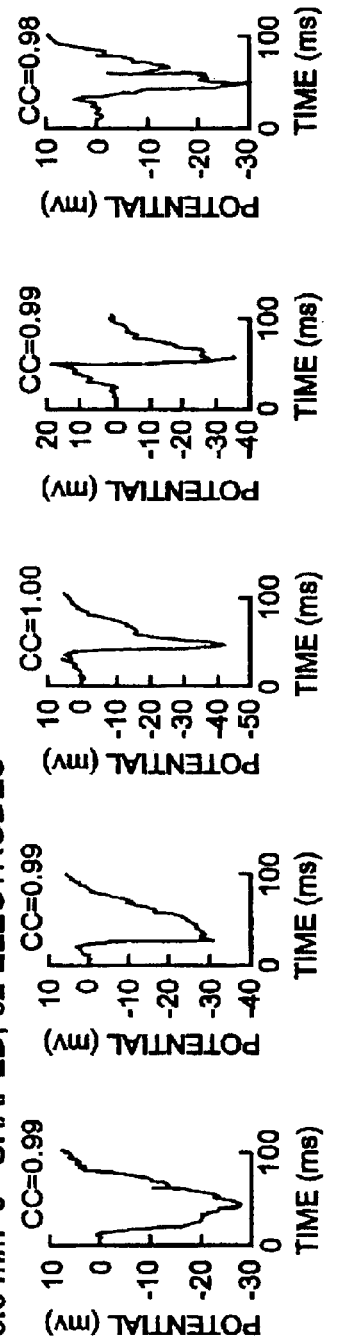

FIG. 10 shows reconstruction of endocardial electrograms from the probes using a subset of 62 electrodes. The cylindrical 7.6 mm probe performs almost as accurately as with 122 electrodes, except for the distant site (site 5). The cylindrical 3.0 mm and curved probes reconstruct 96% of the electrograms with CC greater than 0.90. There are discontinuities ("jagged" appearance or spikes) in some of the computed electrograms, which do not exist in the measured ones. Although the discontinuities cause deterioration of the appearance of the electrograms, the general shapes of the electrograms are preserved. Electrogram at the distant site (site 5) reconstructed from the curved probe resembles the measured electrogram in terms of shape and amplitude. The computed electrograms at a few nodes contain large spikes in certain time frames, the computed electrograms resemble the measured ones very well except during the spikes. The spike can be removed by data interpolation.

Figure 11C:
FIG. 11 includes electrograms showing results obtained using the present invention.
Figure 11D:
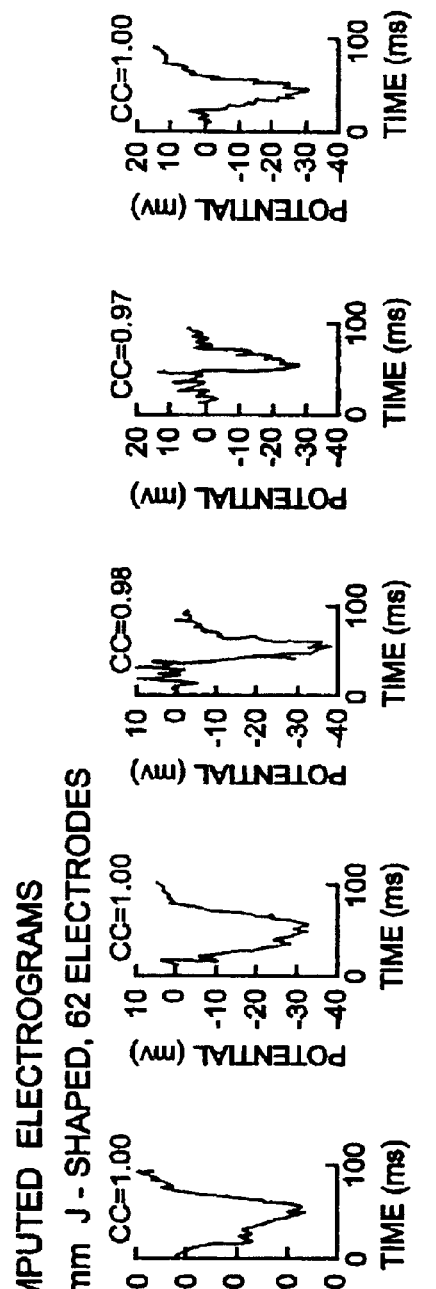

FIG. 11 shows endocardial electrograms reconstructed from the probes with 62 electrodes for a dual-site pacing protocol. The overall performance of the J-probe is most acceptable, with high CC. The distant node electrogram (site 5) is also reconstructed with very high accuracy.

Endocardial isochrones were constructed from both measured and inversely reconstructed endocardial electrograms. FIG. 12 shows the isochrones computed from the reconstructed electrograms of FIG. 9 and FIG. 10. The measured isochrone map is shown in the top panel and the computed isochrone maps in the bottom panels. The position of the earliest activation time in the measured isochrone map is located at the pacing site, indicated by an asterisk (*). The map shows that activation starts at the postero-lateral region and progresses to the anteroseptal region towards the base of the LV. The regions of both earliest activation and latest activation in the measured isochrone map are accurately reconstructed in the computed isochrone map by the 7.6 mm cylindrical and curved catheter with either 122 or 62 electrodes. In contrast, the reconstructed isochrones using the 3.0 mm cylindrical probe with 62 electrodes (second row) exhibit distortion of the earliest activation region, and the latest region (red) divides into two regions. The intermediate isochrones between the earliest and latest activation times in the computed isochrone map closely resemble the measured isochrones for all three probes. The reconstructed earliest activation time (17 ms) is accurate. The latest time of activation reconstructed by the curved catheter with 62 electrodes is 60 ms as compared to the measured value of 63 ms.

FIG. 13 shows the activation sequences (isochrones) initiated by the dual-pacing protocol of FIG. 11. The measured isochrone maps (FIG. 13 top panel) depict two distinct earliest activation regions at the vicinity of the two pacing sites. The earliest activation times determined from the measured electrograms are 18 ms for the two posterior pacing sites. The latest activation region is at the anteroseptal region close to the base of the LV, with activation time of 55 ms. In the isochrone maps computed from the curved catheter with 122 or 62 electrodes (bottom row), the two distinct earliest activation regions are correctly reconstructed. The earliest activation times in the computed isochrone maps are exactly 18 ms. The region of latest activation in the computed isochrone map is located at the anteroseptal region near the base of the LV, in good agreement with its actual location in the measured isochrone map. In contrast, only one of the two early activation sites is present in the reconstructed isochrones obtained from the 7.6 mm and 3.0 mm cylindrical probes.

Figure 14:
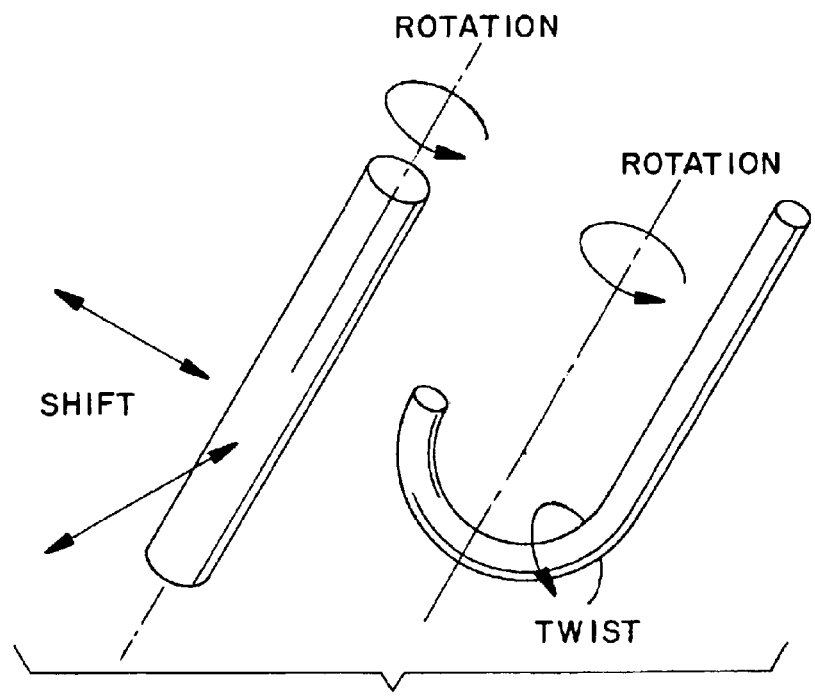
FIG. 14 is an illustration explaining geometric and rotational errors.

Geometrical errors can occur in determining the probe position inside the ventricular cavity. The two most probable errors are shifts and rotations of the probe as a rigid object. For the curved probe, twisting, i.e. rotation about the probe's own axis is also possible. These geometrical errors are illustrated in FIG. 14.

Figure 15C:
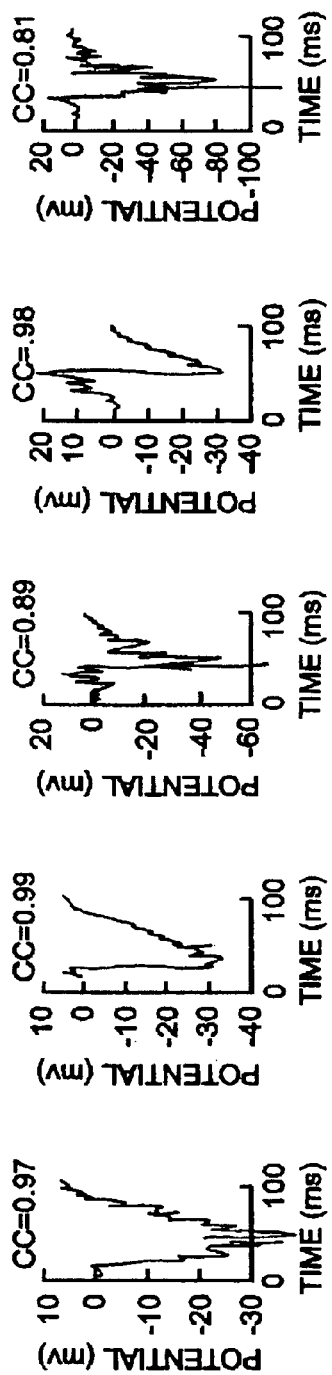
FIG. 15 includes electrograms showing results obtained using the present invention.
Figure 15D:
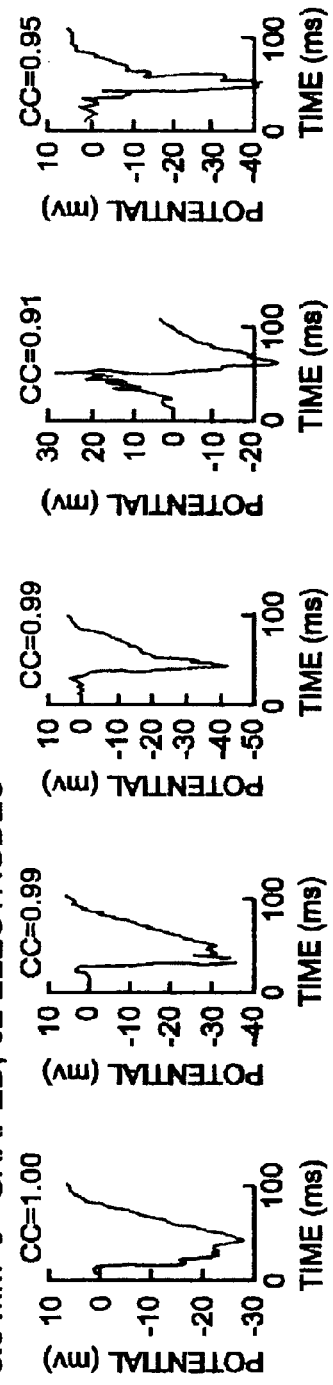

The effects of a 5-degree rotation error on electrogram reconstruction are shown in FIG. 15. All probes used are with 62 electrodes. For the 7.6 mm cylindrical probe, 88% of all the electrograms are reconstructed with CC greater than 0.95. The 3.0 mm cylindrical probe reconstructs 92% of the electrograms with CC greater than 0.95. Of the J-probe reconstructed electrograms, 90% have CC greater than 0.95. It should be noticed that a uniform degree of angular rotation actually results in different position errors for electrodes on the different probes. The 3.0 mm cylindrical probe experiences the smallest distance change, while electrodes on the J-probe "arm" experience the largest position error. This explains why the accuracy of J-probe reconstructions is sensitive to this type of error. In contrast, the 3.0 mm cylindrical probe tolerates the rotational error better than other disturbances.

FIG. 16 shows the isochrones computed from the electrograms of FIG. 15, which demonstrates the effects of a 5-degree angular rotation. FIG. 17 shows the results for 10-degree rotation. Despite the fact that the rotated J-probe has experienced a distance change, it still recovers acceptable activation regions. In the left column of FIG. 17, the J-probe and the 3.0 mm cylindrical probe recover the earliest activation region while the 7.6 mm cylindrical probe does not. In the right column, the J-probe recovers the earliest and latest activation regions with the least pattern deformation compared to the other probes. FIG. 18 shows the effects of probe rotation on a dual-pacing protocol. The 7.6 mm cylindrical probe recovers only one of the two pacing sites; the 3.0 mm cylindrical probe also reconstructs only one (the same) pacing site with greater smoothing. The J-probe identifies the two simultaneous pacing sites with high correlation coefficients of 0.88 for 5 degree rotation and 0.92 for 10 degree rotation.

It has been determined that reconstruction quality under the disturbance of rotation is related to the probe position inside the cavity, more specifically, the position of the J-probe relative to the characteristic sites (pacing site, earliest or latest activation region) influences the reconstruction quality. One possible approach is to simply rotate the same catheter probe in the cavity and record the potentials during two beats, with different rotational positions. Another solution is to introduce a second catheter probe into the cavity with an angle between the two probes, to provide data from two orientations during a single beat. Also as will be shown later, increasing the arm length of the J-probe to form a U-probe helps improve the accuracy of the reconstruction.

Figure 19C:
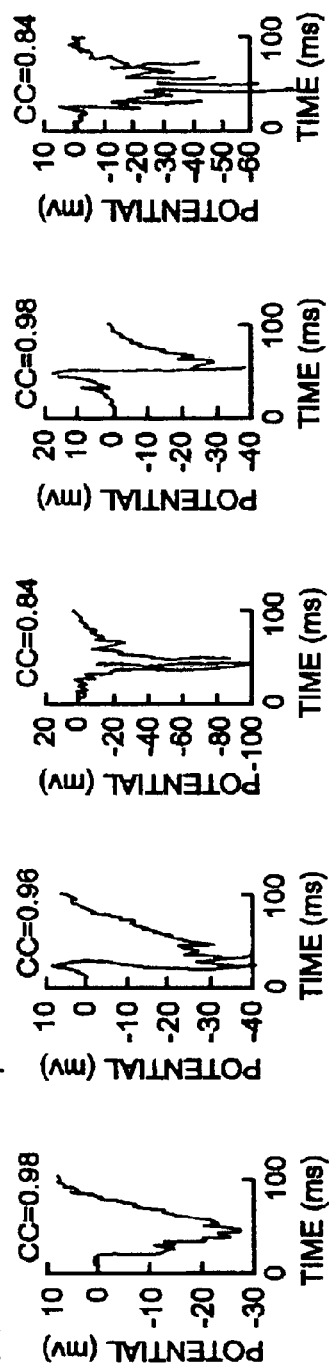
FIG. 19 includes electrograms showing the effects of probe shift on the present invention.
Figure 19D:
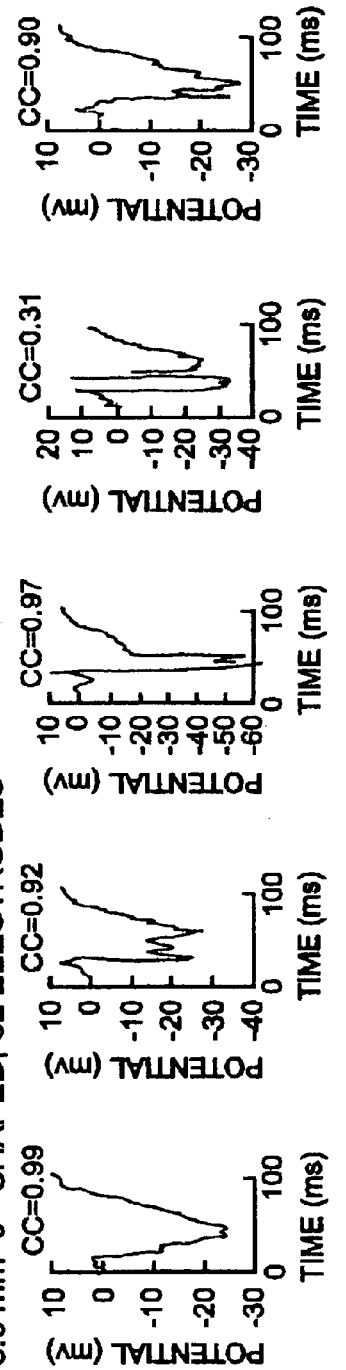
Figure 22A:
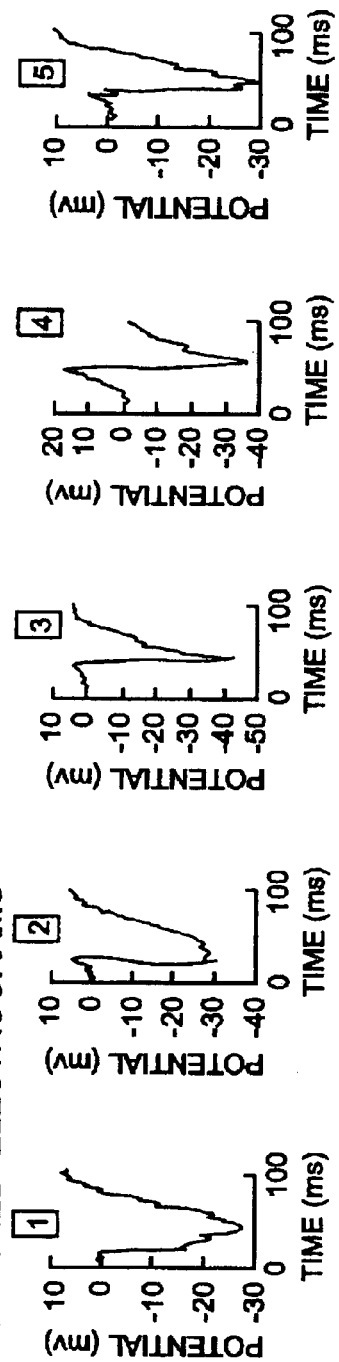
FIG. 22 includes electrograms showing the effects of twisting on the present invention.
Figure 22B:
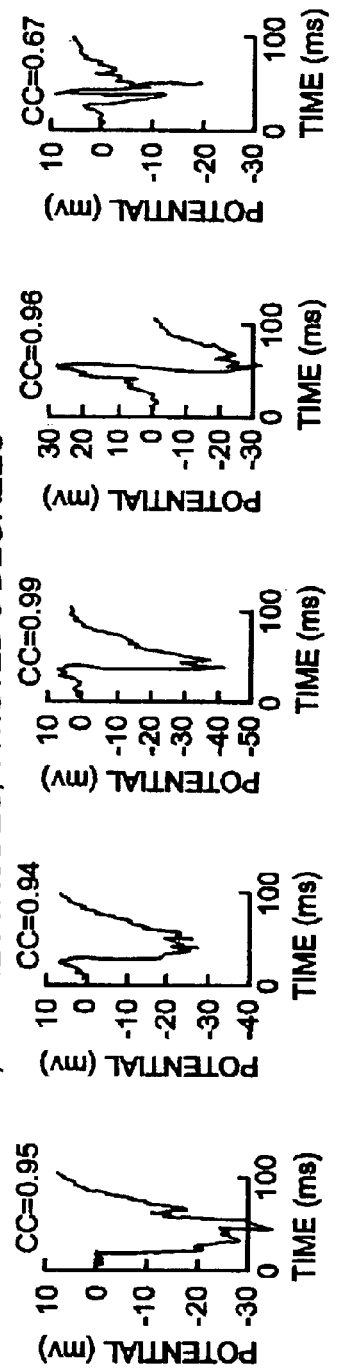
Figure 22C:
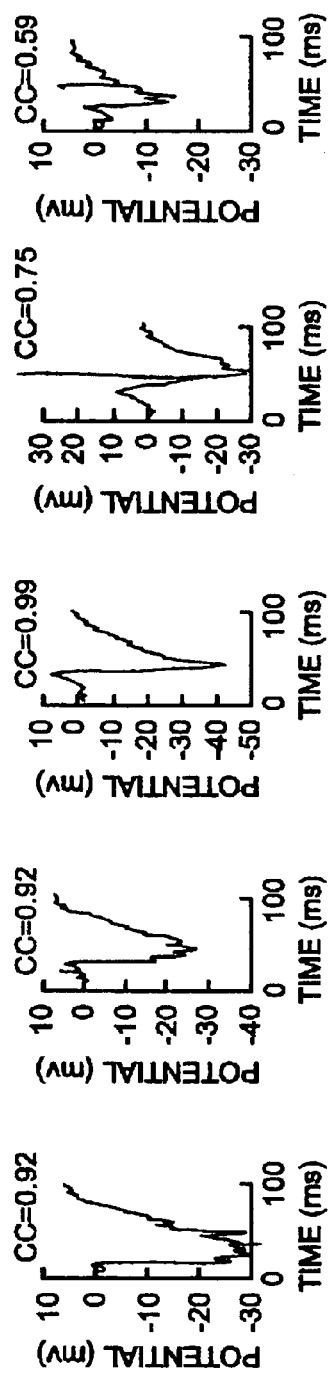
Figure 22D:
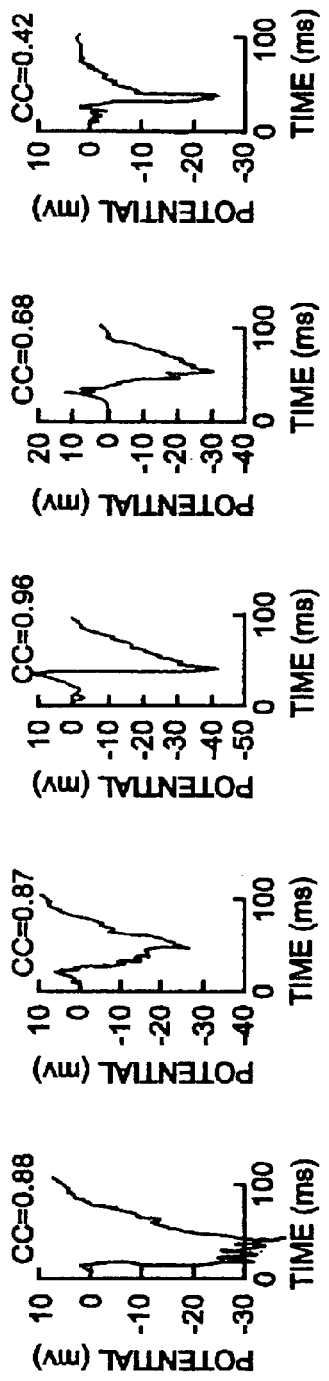

The effects of a shift in probe position on electrogram reconstruction are shown in FIG. 19. Overall, 68% of the recovered electrograms have correlation coefficients higher than 0.90. The 3.0 mm J-probe gives accurately reconstructed electrograms of the early activation sites (column 1, 2, 3) and of the distant node (column 5). However, it fails to accurately recover the latest activation site (column 4), the electrogram is severely distorted.

This is also reflected in the isochronal map of FIG. 20 left column, which is computed from the electrograms of FIG. 19 (2 mm shift). The early activation region is recovered with high accuracy by the 7.6 mm probe and the J-probe. The 3.0 mm cylindrical probe reconstructs the earliest activations site, which has shifted in the lower right direction. The cylindrical probes perform better than the J-probe in the latest activation region. 3 mm shift has the same effects on isochrone reconstruction as shown in FIG. 20, right column. FIG. 21 shows the same simulation for a dual pacing protocol. For 2 mm shift error, the 7.6 mm cylindrical probe reconstructs the earliest region with some distortion. The 3.0 mm cylindrical probe only recovers one of the two pacing sites. The J-probe reconstructs the two earliest activation sites, also with some deformation of patterns in this region. Even for 3 mm shift error, the two earliest activation regions can be distinguished by the J-probe.

It has been determined that the tolerance of the reconstruction to probe shift errors is also related to the position of the probe inside the cavity. If a certain region of the endocardial surface is close to some probe electrodes, the region tolerates better positional errors. The reconstruction quality under the effects of shifting errors can also be improved by using similar approaches as those suggested in the context of the rotation errors.

FIG. 22 shows the electrograms reconstructed from a J-probe with 5 degrees, 10 degrees and 15 degrees twist errors, and FIG. 23 shows the corresponding isochrones. Electrograms display significant morphological distortions in most of the nodes. For 5 and 10 degrees twist, even with major morphological changes in the electrograms, the isochrones still recover the earliest activation region and the latest activation region (although the latter is smoothed out). Under 15 degrees twist, the latest activation region is completely smoothed out. For the dual-pacing protocol, the J-probe with 5 degrees twist can still identify the two earliest activation sites accurately. Under higher twist error, the two pacing sites merge together and can not be separated.

Figure 24C:
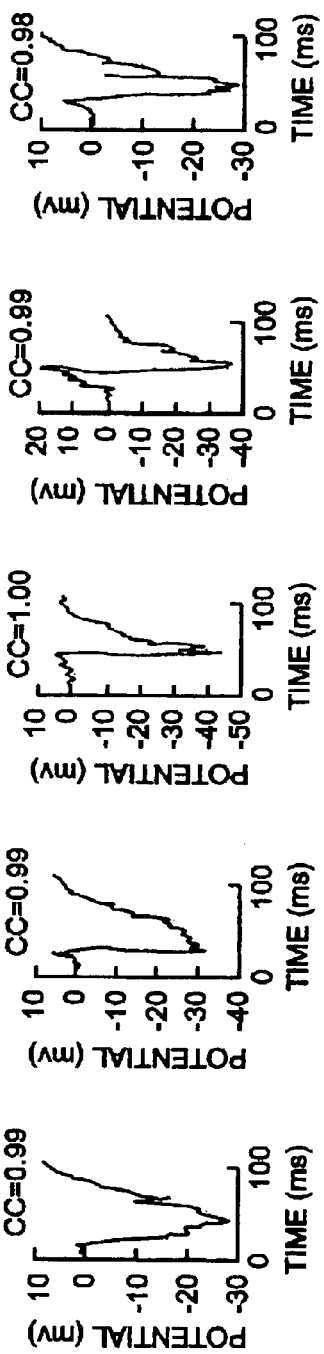
FIG. 24 includes electrograms showing the effects of catheter probe shape on the present invention.
Figure 24D:
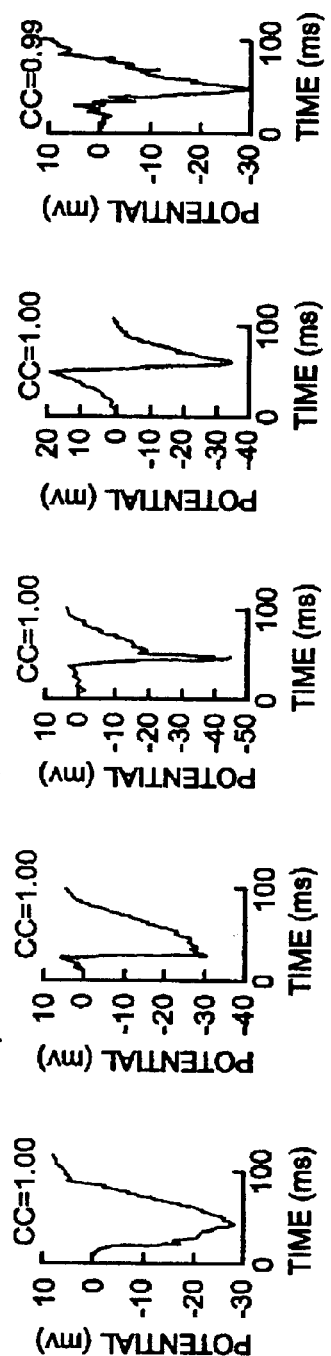
Figure 27:
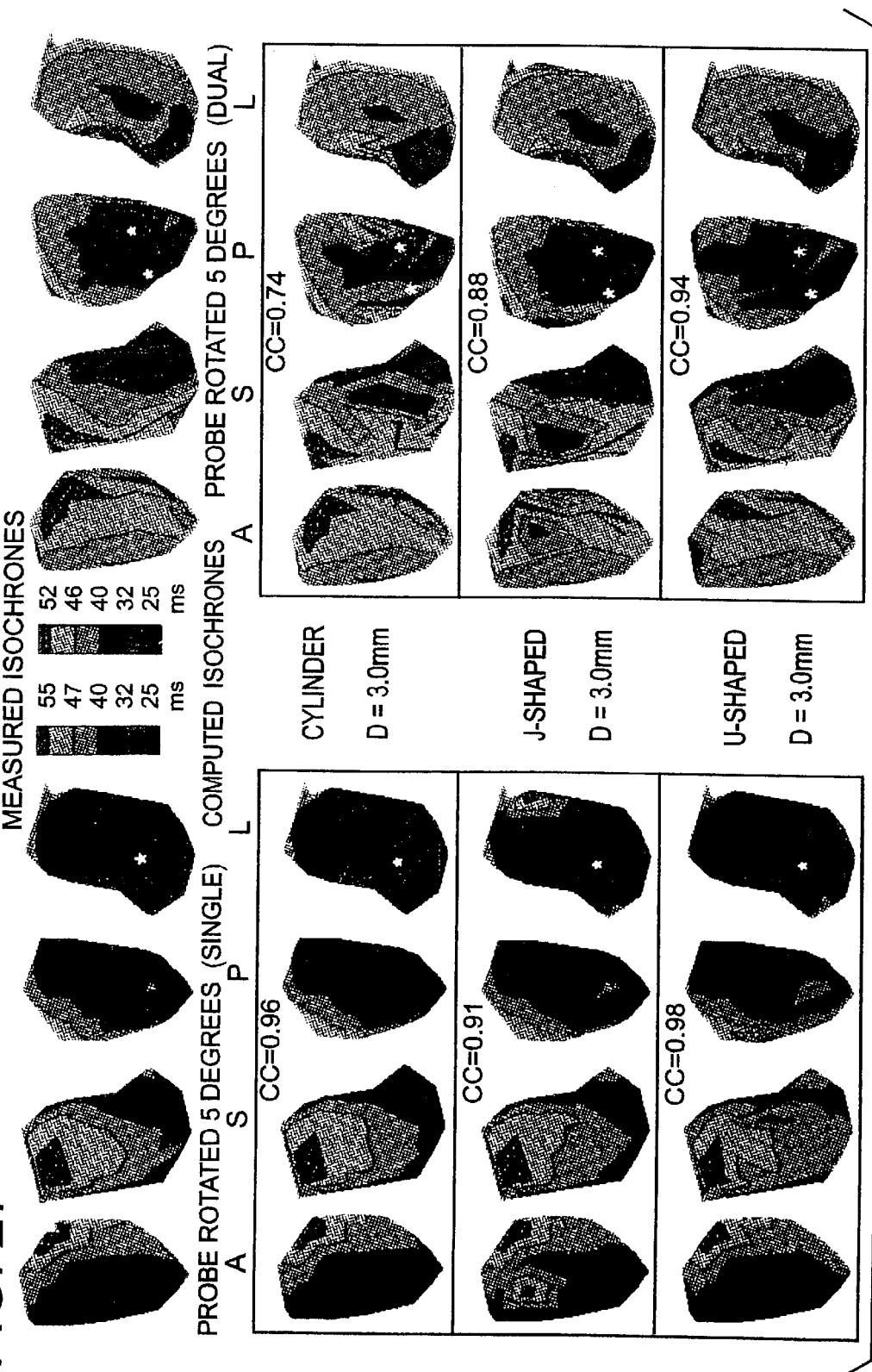
FIG. 27 includes isochrone maps showing the effects of catheter shape on the present invention.
Figure 28:
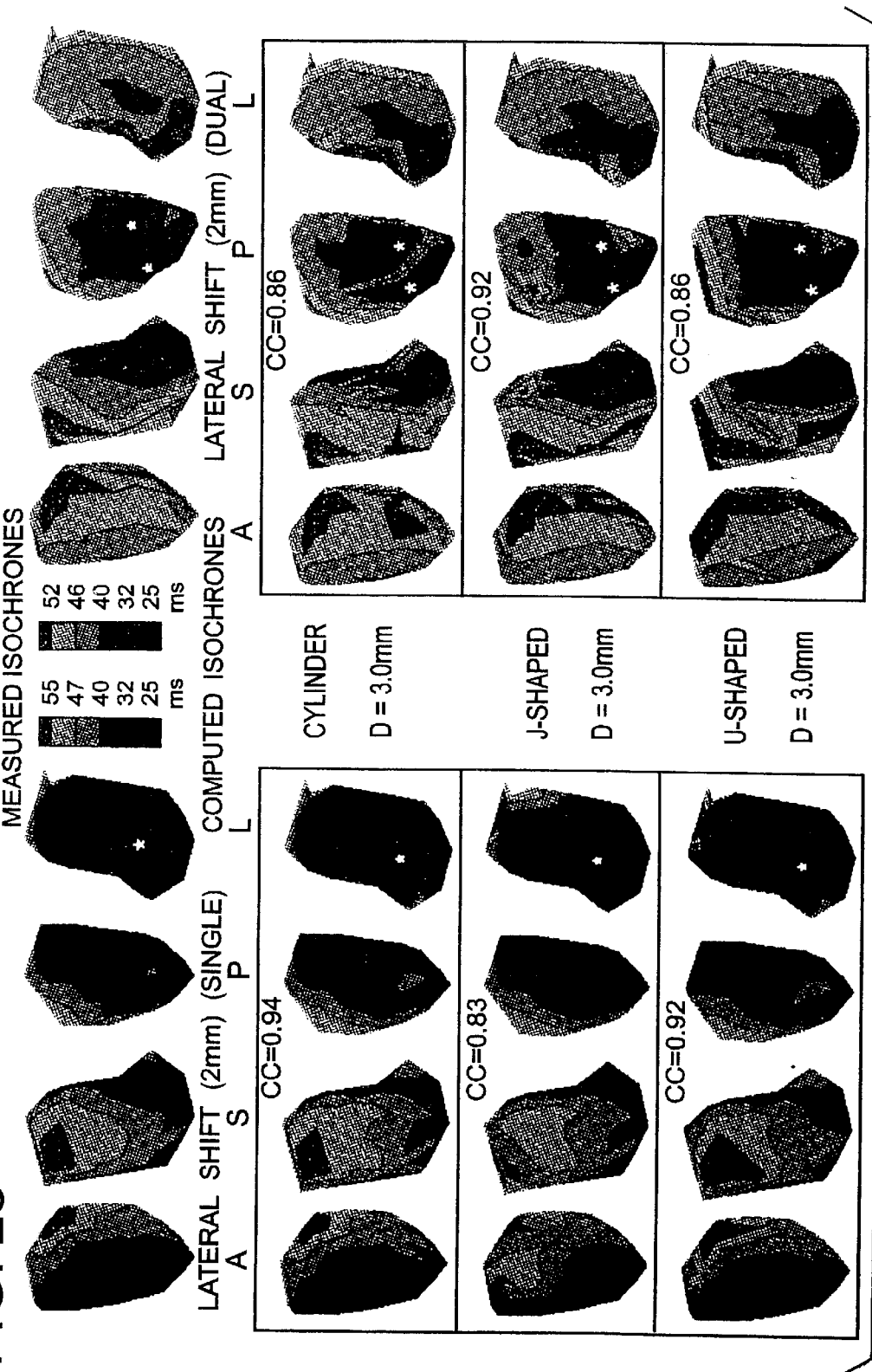
FIG. 28 includes isochrone maps showing the effects of catheter shape on the present invention.

The J-probe used in this simulation study is characterized by a relatively short arm, as shown in FIG. 3. It serves to represent a large variety of curved catheter probes with either different curvature or other shapes, such as "U", or "O", or any curved shape. In order to evaluate the effects of different catheter shapes on the reconstruction quality, simulations for a U-shaped catheter probe (FIG. 4) have also been conducted. FIG. 24 shows the electrograms reconstructed from the 3.0 mm probe, the J-probe and a 3.0 mm U-probe also with 62 electrodes. The U-probe has the same curvature as the J-probe. Note that the computed electrograms from the 3.0 mm cylindrical and J-probe are the same as shown in FIG. 10. From the cylindrical probe to the U-probe, the accuracy of the reconstruction progressively improves with the length of the "arm". The U-probe reconstructs the electrograms with very high accuracy, without any discontinuities or spikes. FIG. 25 left column shows the isochrones computed from the electrograms of FIG. 24. The improvement in the latest activation region of the isochrones reconstructed by the U-probe is evident. The right column of FIG. 25 shows the reconstructed isochrones from the three catheter probes with only 42 electrodes. The 3.0 mm cylindrical and J-shaped probes fail to recover the earliest activation region, however, the U-probe still accurately reconstructs both the earliest and latest activation regions. Reconstructed isochrones for the dual pacing protocol from the catheter probes are shown in FIG. 26. Only the U-probe, with either 62 or 42 electrodes, recovers the two distinct earliest activation regions accurately. FIG. 27 shows the reconstructed isochrones from the catheters under 5-degree rotation error. The performance of the U-probe is comparable or relatively better than the J-probe. Similarly, FIG. 28 shows the reconstructed isochrones from the catheters under 2 mm shift error. In the single pacing case (left column), the U-probe is the only one that recovers both the earliest and latest activation regions.

The results from the present study indicate that a noncontact, nonexpandable, miniature multielectrode catheter is useful for cardiac mapping. Although curving the catheter is not necessary to obtain relatively accurate results, such curving results in improved results in many respects. As is apparent from the above data, although a large number of electrodes is desirable when we consider the quality of the inverse reconstruction, it may raise other issues in design and manufacturing of the probe and the data acquisition system. Thus, for a J-probe, 60 probe electrodes or more is desirable because it reconstructed the endocardial electrograms and isochrones with good accuracy. However, the U-probe was found to tolerate reduced electrode number down to 42 very well.

The above description merely provides a disclosure of particular embodiments of the invention and is not intended for the purpose for limiting the same thereto. As such, the invention is not limited to only the above described embodiments. Rather, it is recognized that one skilled in the art could conceive alternative embodiments that fall within the scope of the invention.

I claim:

1. A system for determining electrical potentials on an endocardial surface of a heart, the system comprising:
   a non-contact catheter probe having a surface and a terminal end portion adapted to be positioned in a cavity of the heart, the terminal end portion being adapted to be conformed into a first elongate shape and at least one second curved shape that includes a spiral shape, wherein the terminal end portion is conformed without expanding the terminal end portion;
   a plurality of electrodes disposed on the end portion of the probe, the electrodes being adaptable to measure electrical potentials in the cavity;
   imaging means for capturing geometric data on the probe and the endocardial surface;
   means for determining a geometric relationship between the probe surface and the endocardial surface based on the geometric data;
   means for generating a matrix of coefficients representing the geometric relationship between the probe surface and the endocardial surface; and,
   means for determining endocardial potentials based on catheter probe electrode potentials and the matrix of coefficients.

2. The system as set forth in claim 1 wherein the second curved shape resembles one of a pigtail and a helix.

3. The system as set forth in claim 1 wherein the probe includes means for conforming the terminal end portion of the probe to the first elongate shape while being positioned in the cavity and means for conforming the terminal end portion of the probe into the second curved shape once in the cavity.

4. A system as set forth in claim 1, where the terminal end includes a cylindrical cross-section.

5. A system as set for the in claim 1, where means for determining endocardial potentials include means for reconstructing endocardial potentials throughout the endocardial surface on a beat-by-beat basis.

6. A system according to claim 1, further comprising at least one of:

means for generating electrograms based on the determined endocardial potentials; and, means for generating isochrone maps based on the electrograms.

7. A system for determining electrical potentials on an endocardial surface of a heart, the system comprising:

a non-contact catheter probe having a surface and a terminal end portion adapted to be positioned in a cavity of the heart, the terminal end portion being cylindrical in cross-section and adapted to be conformed into a first elongate shape and at least one second curved shape that includes a spiral shape, wherein the terminal end portion is conformed without expanding the terminal end portion;

a plurality of electrodes disposed on the end portion of the probe, the electrodes being adaptable to measure electrical potentials in the cavity;

imaging means for capturing geometric data on the probe and the endocardial surface;

means for determining a geometric relationship between the probe surface and the endocardial surface based on the geometric data;

means for generating a matrix of coefficients representing the geometric relationship between the probe surface and the endocardial surface;

means for determining endocardial potentials based on catheter probe electrode potentials and the matrix of coefficients;

means for generating electrograms based on the determined endocardial potentials; and, means for generating isochrone maps based on the electrograms.

8. The system as set forth in claim 7 wherein the second curved shape resembles one of a pigtail and a helix.

9. The system as set forth in claim 7 wherein the probe includes means for conforming the terminal end portion of the probe to the first elongate shape while being positioned in the cavity and means for conforming the terminal end portion of the probe into the second curved shape once in the cavity.

10. A system according to claim 7, further comprising at least one of:

means for generating electrograms based on the determined endocardial potentials; and, means for generating isochrone maps based on the electrograms.

11. A system for determining electrical potentials on an endocardial surface of a heart, the system comprising:

a non-contact catheter probe means, having a surface and a terminal end portion, for position in a cavity of the heart, the terminal end portion being cylindrical in cross-section and adapted to be conformed into a first elongate shape and at least one second curved shape that includes a spiral shape, wherein the terminal end portion is conformed without expanding the terminal end portion;

electrode means disposed on the end portion of the probe, for measuring electrical potentials;

imaging means for capturing geometric data on the probe and the endocardial surface;

means for determining a geometric relationship between the surface of the probe means and the endocardial surface based on the geometric data;

means for generating a matrix of coefficients representing the geometric relationship between the surface of the probe means and the endocardial surface;

means for determining endocardial potentials based on catheter probe electrode potentials and the matrix of coefficients;

means for generating electrograms based on the determined endocardial potentials; and, means for generating isochrone maps based on the electrograms.

12. A system according to claim 11, further comprising at least one of:

means for generating electrograms based on the determined endocardial potentials; and, means for generating isochrone maps based on the electrograms.

\* \* \* \* \*